United States Patent
Batman et al.

(10) Patent No.: US 7,401,111 B1
(45) Date of Patent: Jul. 15, 2008

(54) INSTRUMENT SETUP UTILITY PROGRAM

(75) Inventors: Carol Jane Batman, Indianapolis, IN (US); Nancy Kennedy Byrd, Indianapolis, IN (US); Timothy J. Dishop, Fort Wayne, IN (US); Les G Henderson, Cicero, IN (US); Patricia A. Hopkinson, Lake Placid, NY (US); Stephen E. Moak, Fort Wayne, IN (US); James R. Parker, Carmel, IN (US); Frank M. Polaski, Fort Wayne, IN (US); Atwell R. Shearer, Rome City, IN (US); Tracy Knudsen, Pittsburgh, PA (US); Lynne Denise Sly, Fishers, IN (US); Kurt Gerard Klem, Indianapolis, IN (US)

(73) Assignee: Roche Diagnostic Operations, Inc., Indianapolis, IN (US)

(*) Notice: Subject to any disclaimer, the term of this patent is extended or adjusted under 35 U.S.C. 154(b) by 0 days.

(21) Appl. No.: 09/555,718

(22) PCT Filed: Dec. 4, 1998

(86) PCT No.: PCT/US98/25850

§ 371 (c)(1),
(2), (4) Date: Jan. 12, 2001

(87) PCT Pub. No.: WO99/27849

PCT Pub. Date: Jun. 10, 1999

Related U.S. Application Data

(60) Provisional application No. 60/067,499, filed on Dec. 4, 1997.

(51) Int. Cl.
*G06F 15/16* (2006.01)
(52) U.S. Cl. ................................ 709/200; 600/300
(58) Field of Classification Search ................ 709/200, 709/203, 223, 224; 379/106; 340/573, 870, 340/825; 600/300, 301, 508; 607/46, 60, 607/48; 705/2
See application file for complete search history.

(56) References Cited

U.S. PATENT DOCUMENTS 4,370,983 A * 2/1983 Lichtenstein ................ 600/301
4,383,534 A   5/1983 Peters (Continued)

OTHER PUBLICATIONS

Chap8p1—Converted; www.vandersluis.net/book/Chap8.html.*

(Continued)

*Primary Examiner*—Thong H Vu
(74) *Attorney, Agent, or Firm*—Barnes & Thornburg LLP

(57) ABSTRACT

A method of configuring a hand-held instrument (10) for determining the concentration of a medically significant component of a body fluid or a control comprises providing a configuring computer (14) having a first port (18) for transmitting instructions and data for configuring the instrument (10), providing on the instrument (10) a second port (17) for receiving the instructions and data from the configuring computer (14), coupling the first port (18) to the second port (17), transmitting instructions and data to configure the instrument (10) from the first port (18), receiving the instructions and data at the second port (17), and configuring the instrument (10) according to the instructions and data transmitted from the first port (10) and received at the second port (17).

32 Claims, 44 Drawing Sheets

U.S. PATENT DOCUMENTS

| | | | | |
|---|---|---|---|---|
| 4,637,403 | A | | 1/1987 | Garcia |
| 4,696,309 | A | | 9/1987 | Stephan |
| 5,113,869 | A | * | 5/1992 | Nappholz et al. ............ 600/508 |
| 5,307,263 | A | * | 4/1994 | Brown ......................... 600/301 |
| 5,361,336 | A | | 11/1994 | Atchison |
| 5,368,562 | A | | 11/1994 | Blomquist |
| 5,570,682 | A | | 11/1996 | Johnson |
| 5,606,164 | A | | 2/1997 | Price et al. |
| 5,619,991 | A | | 4/1997 | Sloane |
| 5,630,664 | A | * | 5/1997 | Farrelly ....................... 600/508 |
| 5,724,983 | A | | 3/1998 | Selker |
| 5,735,285 | A | | 4/1998 | Albert |
| 5,827,180 | A | * | 10/1998 | Goodman .................... 600/300 |
| 5,846,224 | A | * | 12/1998 | Sword et al. ................. 604/113 |
| 5,889,474 | A | * | 3/1999 | LaDue .................. 340/825.49 |
| 5,944,659 | A | * | 8/1999 | Flach et al. .................. 600/300 |
| 5,974,124 | A | * | 10/1999 | Schlueter et al. ........ 379/106.02 |
| 5,997,476 | A | * | 12/1999 | Brown ......................... 600/300 |
| 6,072,396 | A | * | 6/2000 | Gaukel ..................... 340/573.4 |
| 6,186,145 | B1 | * | 2/2001 | Brown ......................... 600/300 |
| 6,408,330 | B1 | * | 6/2002 | DeLaHuerga .............. 709/217 |
| 6,427,088 | B1 | * | 7/2002 | Bowman et al. .............. 607/60 |
| 6,441,747 | B1 | * | 8/2002 | Khair et al. ............ 340/870.16 |
| 6,516,227 | B1 | * | 2/2003 | Meadows et al. ............. 607/46 |
| 6,673,596 | B1 | * | 1/2004 | Sayler et al. ............. 435/288.7 |
| 7,114,502 | B2 | * | 10/2006 | Schulman et al. ........... 128/899 |
| 2002/0169636 | A1 | * | 11/2002 | Eggers et al. ................... 705/3 |
| 2003/0229514 | A2 | * | 12/2003 | Brown ........................... 705/2 |
| 2005/0104577 | A1 | * | 5/2005 | Matei et al. ............ 324/207.13 |
| 2005/0137648 | A1 | * | 6/2005 | Cosendai et al. ............. 607/48 |

OTHER PUBLICATIONS

Information technology resources to support persons involved with diabetes; www.lehigh.edu/lists/diabetic/html/software.html.*
Automated measurement of retinal vascular tortuosity—Hart, Goldbaum (1997) ; ftp.cs.sandia.gov/pub/papers/wehart/1997/HarGolCotKubNel97-amia.ps.gz.*
Temporal Abstractions for Diabetic Patients Management—Cristiana Larizza (1997) ; aim.unipv.it/pub/papers/larizza/aime97.ps.gz.*
Clinical Applications of Palmtop Computing Annotated Bibliography www.cs.umbc.edu/~mikeg/palm.html.*
[1997] Lightweight, Mobile E-Mail for Intra-Clinic Communication www.amia.org/pubs/symposia/D004447.PDF.*
Securing Radio Spectrum for Wireless Internet Access www.isoc.org/isoc/whatis/conferences/inet/96/proceedings/g1/g1_4.htm.*

* cited by examiner

Fig. 6

Meter Setup Wizard - Glucose Units/Ranges

Units of Measure
Glucose: ● mg/dL   ○ mmol/L

Glucose Limits
Upper Limit: [ 0 ]   mg/dL
Lower Limit: [ 0 ]   mg/dL
Hypo: [ 0 ]   mg/dL

[ < Back ]  [ Next > ]   [ Cancel ]  [ Help ]

Fig. 7

Meter Setup Wizard - Insulin Type

Select up to three Insulin Types. These will be the only types available in the meter.

Check the Insulin Logging box if you want to record insulin information in your meter.

☐ Insulin Logging Enabled for Meter Setup

Insulin Types
Insulin Type 1:   Insulin Type 2:   Insulin Type 3:
[ <None> ▼ ]   [ <None> ▼ ]   [ <None> ▼ ]

Insulin Increment:
● Tenth Unit   ○ Half Unit   ○ Whole Unit

[ < Back ]  [ Next > ]   [ Cancel ]  [ Help ]

Meter Setup Wizard - Time Blocks

Time Block information is contained in the list below.

The minimum time span for a Time Block is 1/2 hour. Editing the start time of a Time Block automatically adjusts the end time of the previous Time Block. No Time gaps are allowed between Time Blocks.

To edit an existing Time Block, select the Time Block and press the Edit button, or double click on the Time Block entry in the list.

| Time Block Name | 3 Letter Name | Start Time | End Time | Duration |
|---|---|---|---|---|
| Breakfast | Brk | 6:00 AM | 8:59 AM | 3.0 |
| Midmorning | Mmo | 9:00 AM | 11:59 AM | 3.0 |
| Lunch | Lun | 12:00 PM | 2:59 PM | 3.0 |
| Midafternoon | Maf | 3:00 PM | 5:59 PM | 3.0 |
| Dinner | Din | 6:00 PM | 7:59 PM | 2.0 |
| Evening | Eve | 8:00 PM | 9:59 PM | 2.0 |
| Bed time | Bed | 10:00 PM | 2:59 AM | 5.0 |
| Night time | Ngt | 3:00 AM | 5:59 AM | 3.0 |

[ Edit... ]

[ < Back ] [ Next > ]   [ Cancel ]   [ Help ]

Meter Setup Wizard - Event Markers

Select up to 15 Event Markers to add to the Meter Setup

The Events will appear in the meter in the order they appear in the 'Events To Load Into Meter' list.

You have selected 15 Events

| S | Available Events | | Events to Load into Meter |
|---|---|---|---|
|   | Active | | Before Meal |
|   | After Breakfast | | After Meal |
|   | After Dinner | | Fasting |
| ✓ | After Exercise | | Snack |
| ✓ | After Lunch | [ Add > ] | Feel Hypo. |
| ✓ | After Meal | | Before Exercise |
|   | Bed Time | [ < Remove ] | After Exercise |
|   | Before Breakfast | | Illness |
|   | Before Dinner | | Invalid Test |
| ✓ | Before Exercise | | Other's Result |
|   | Before Lunch | | User Defined |
| ✓ | Before Meal | | Stress |
|   | Cold Outdoors | | L1 Control |
|   | Different Food | | L2 Control |
|   | Drank Alcohol | | Oral Medication |

S = Selected Event Markers

[ < Back ] [ Next > ]   [ Cancel ]   [ Help ]

```
Time Block Information                              [X]

Three Letter Name:  Brk

Start time:  [6:00] AM [▲▼]  End Time: 8:59 AM

┌─Customize Time Block─────────────────────────┐
   │ Insulin Type 1: <None>    Dose  [0.0]         │
   │ Insulin Type 2: <None>    Dose  [0.0]         │
   │ Insulin Type 3: <None>    Dose  [0.0]         │
   │                                               │
   │ Exercise Type: [<None> ▼] Duration: [0.00 ▲▼] │
   │                                               │
   │ Carbohydrates: [0]   grams                    │
   │                                               │
   │ Event 1: [No Event ▼]  Event 3: [No Event ▼]  │
   │ Event 2: [No Event ▼]  Event 4: [No Event ▼]  │
   └───────────────────────────────────────────────┘

[ OK ]   [ Cancel ]   [ Help ]
```

Fig. 11

```
Meter Setup Wizard - Insulin Pump Profile

Check the Insulin Pump Logging box is you want
to record Insulin Pump Information in your meter:

[ ]  Insulin Pump Logging Enabled in Meter Setup

Type of Insulin: [<None> ▼]

Profile Start Date [11/09/98 ▲▼]  Profile Start Time [2:50 PM ▲▼]

┌──────────────┬───────────┬──────────┬───────────┐
│Time Block Name│Start Time│ End Time │ Pump Rate │
├──────────────┼───────────┼──────────┼───────────┤
│Time Block #1 │ 12:00 AM  │ 11:59 PM │   0.0     │
│              │           │          │           │
└──────────────┴───────────┴──────────┴───────────┘

[ Insert ]  [ Edit... ]  [ Delete ]
─────────────────────────────────────────────────────

[ < Back ]  [ Next > ]  [ Cancel ]  [ Help ]
```

Fig. 14

Meter Setup Wizard - Misc. Options

Select the appropriate Meter Customization Options

Decimal Format
- ○ Comma [,]
- ⊙ Period [.]

Time Format
- ○ 24 Hour
- ⊙ 12 Hour

Date Format
- ○ dd-mm-yy
- ⊙ mm-dd-yy

Meter Back Light
- ○ Off
- ⊙ On

Beeper
- ○ Off
- ⊙ On

[< Back] [Next >] [Cancel] [Help]

Meter Setup Wizard - Languages

Select four Languages for the Meter Setup.

Languages
- ☐ Dutch
- ☑ English
- ☑ French
- ☑ German
- ☐ Italian
- ☑ Spanish
- ☐ Swedish

[< Back] [Next >] [Cancel] [Help]

| Print Patient Report | | | X |
|---|---|---|---|
| Patient Name | Serial number | Received | |
| John Smith | 0005040225 | | |

File Path:

[ Print ]
[ Cancel ]
[ Browse... ] [ Help ]

*Fig. 35*

| | | -Patient Data Report | | | · ☐ X |
|---|---|---|---|---|---|
| Close | Print | Settings... | Help | | |

Transfer Date/Time:  11/10/98   7:28  AM
Meter Serial Number: 0005040225
Patient Name         John Smith
Patient ID           default Diary Report

| Date | Time | Glucose (mg/dL) | Insulin Type | Insulin Dosage | Events | Other |
|---|---|---|---|---|---|---|
| 1/16/98 | 7:30 AM | 236 | 70/30 | 22.0 | Before Meal | bG=high, Carbs=60g |
| 1/16/98 | 12:28 PM | 85 | | | Before Meal | Carbs=60g |
| 1/16/98 | 2:45 PM | 179 | | | After Meal | Carbs=30g |
| 1/16/98 | 5:20 PM | 314 | Reg 70/30 | 2.0 8.0 | Before Meal | bG=high, Carbs=60g |
| 1/16/98 | 8:00 PM | 250 | | | | bG=high |
| 1/17/98 | 12:15 AM | 275 | | | | bG=high |
| 1/17/98 | 7:58 AM | 151 | 70/30 | 22.0 | Before Meal | Carbs=45g |
| 1/17/98 | 10:00 AM | 180 | | | After Meal | Carbs=15g |

*Fig. 53*

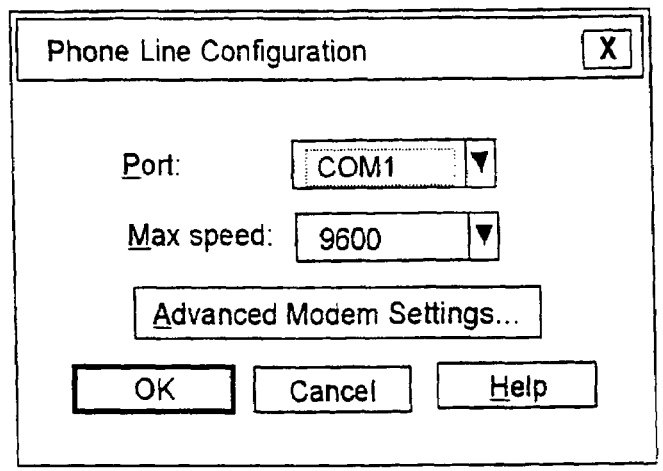
Fig. 56
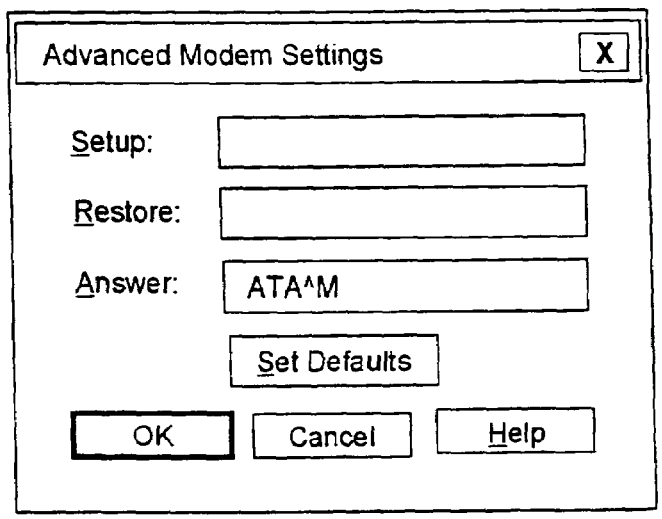
Fig. 57
Fig. 58

INSTRUMENT SETUP UTILITY PROGRAM

CROSS-REFERENCES TO RELATED APPLICATIONS

This application is a U.S. national counterpart application of international application Ser. No. PCT/US98/25850 filed Dec. 4, 1998, which claims priority to U.S. provisional application Ser. No. 60/067,499 filed Dec. 4, 1997.

This is a related application to U.S. Ser. No. 60/067,512, titled INSTRUMENT, filed Dec. 4, 1997, U.S. Ser. No. 60/067,499, filed Dec. 4, 1997, titled INSTRUMENT SETUP UTILITY PROGRAM, and U.S. Pat. No. 6,635,167, titled APPARATUS AND METHOD FOR DETERMINING THE CONCENTRATION OF A COMPONENT OF A SAMPLE, issued Oct. 21, 2003, filed on the same date as this application. These related applications are assigned to the same assignee as this application. The disclosures of those applications are incorporated herein by reference.

FIELD OF THE INVENTION

This invention relates to a utility program useful in, for example, the setup of, and communication with, instruments of the general type described in U.S. Pat. No. 6,635,167.

DISCLOSURE OF THE INVENTION

A method of configuring a hand-held instrument for determining the concentration of a medically significant component of a body fluid or a control comprises the steps of providing a configuring computer having a first port for transmitting at least one of instructions and data for configuring the instrument, providing on the instrument a second port for receiving said at least one of instructions and data from the configuring computer, coupling said first port to said second port, transmitting said one of instructions and data to configure said instrument from said first port, receiving said one of instructions and data at said second port, and configuring said instrument according to said one of instructions and data transmitted from said first port and received at said second port.

Illustratively according to the invention, the step of providing a configuring computer having a first port for transmitting at least one of instructions and data for configuring the instrument comprises the step of providing a configuring computer having a first port for transmitting instructions for configuring the instrument.

Further illustratively according to the invention, the step of providing a configuring computer having a first port for transmitting at least one of instructions and data for configuring the instrument comprises the step of providing a configuring computer having a first port for transmitting data for configuring the instrument.

Additionally illustratively according to the invention, the hand-held instrument further comprises a display for displaying information related to the determined concentration. The step of transmitting said one of instructions and data to configure said instrument from said first port comprises the step of transmitting said one of instructions and data from said first port to configure said display.

Illustratively according to the invention, the method further comprises the step of transmitting one of instructions and data concerning determined concentration of a medically significant component of a body fluid from the second port to the first port.

Further illustratively according to the invention, the step of transmitting one of instructions and data concerning determined concentration of a medically significant component of a body fluid from the second port to the first port comprises the step of transmitting data concerning determined concentration of a medically significant component of a body fluid from the instrument to the computer.

Additionally illustratively according to the invention, the method further comprises updating a file in the computer with the transmitted data.

Illustratively according to the invention, the steps of transmitting said one of instructions and data to configure said instrument from said first port and receiving said one of instructions and data at said second port comprise transmitting said one of instructions and data through a fiber optic coupler from said first port to said second port.

Further illustratively according to the invention, the instrument comprises an instrument for determining the glucose concentration of blood, a blood fraction or a control.

Additionally illustratively according to the invention, the step of transmitting said one of instructions and data concerning determined concentration of a medically significant component of a body fluid from the second port to the first port comprises the step of transmitting said one of instructions and data concerning determined concentration of a medically significant component of a body fluid via a modem from the second port to the first port.

BRIEF DESCRIPTION OF THE DRAWINGS

The invention may best be understood by referring to the following detailed descriptions of illustrative embodiments and the accompanying drawings. In the drawings.

DETAILED DESCRIPTIONS OF ILLUSTRATIVE EMBODIMENTS

Figure 1:
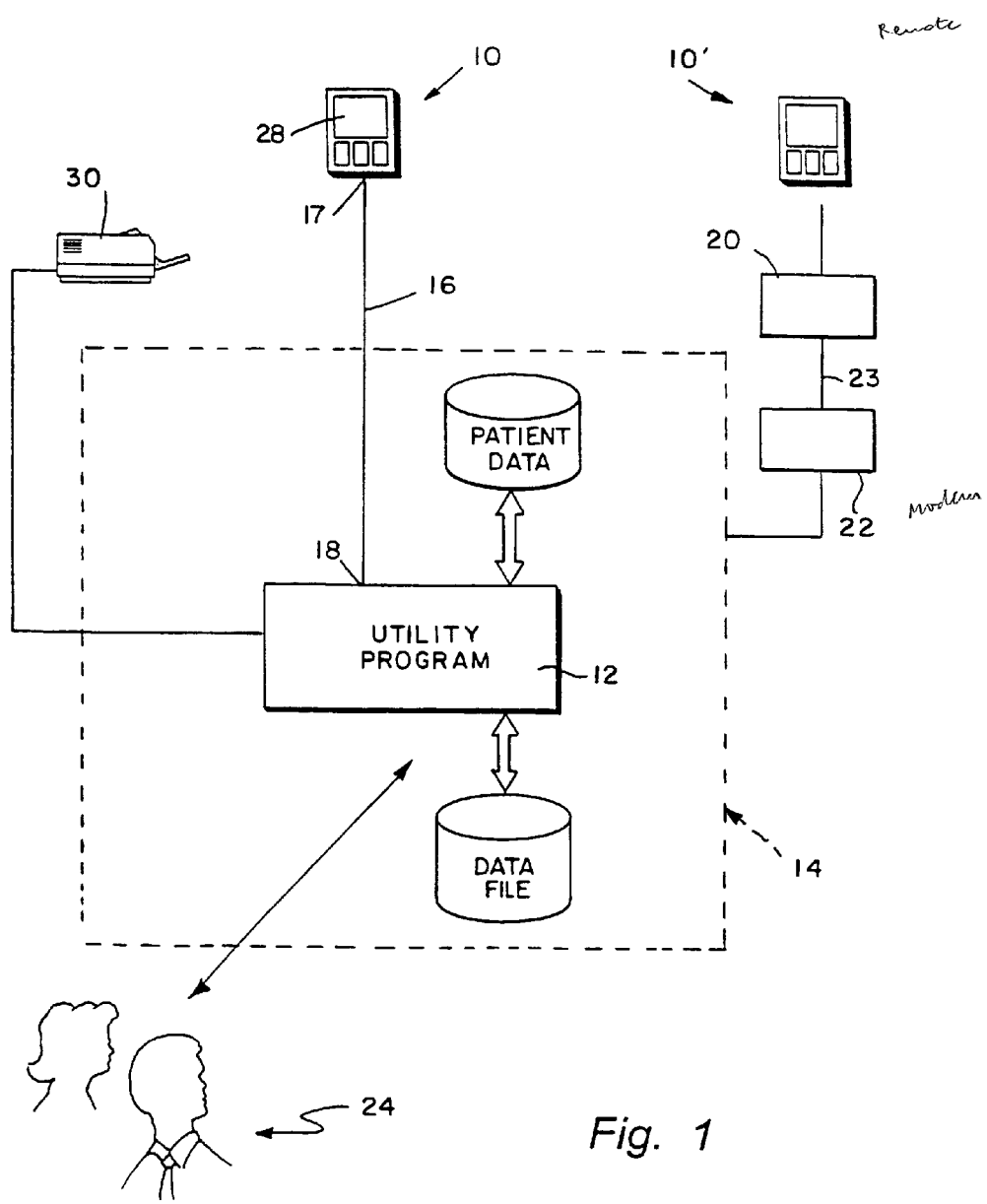
FIG. 1 illustrates a diagram of a system implementing a utility program according to the present invention.

This invention relates to a utility program useful in, for example, the setup of, and communication with, instruments of the general type described in the above-mentioned U.S. Pat. No. 6,635,167, which is hereby incorporated by reference herein. FIG. 1 illustrates diagrammatically a system implementing the utility program 12 of the present invention. Setup of such an instrument 10 is handled by a portion of the program 12 sometimes referred to hereinafter as a Meter Setup Manager through a docking station provided for the instrument 10 on a personal computer (PC) 14. Communication between the docked instrument 10 and the PC 14 is coupled through a serial cable 16 such as, for example, a fiber optic connector, from a port 17 on instrument 10 to a port 18 on the PC 14. Communication with a remote instrument 10', such as for the downloading of test results from storage on board the instrument 10' to the PC 14, is handled by a portion of the program sometimes referred to hereinafter as a Phone-In Manager. Phone-In Manager is conducted via telephone modems 20, 22 at the remote instrument 10' site and the PC 14.

Figure 2:
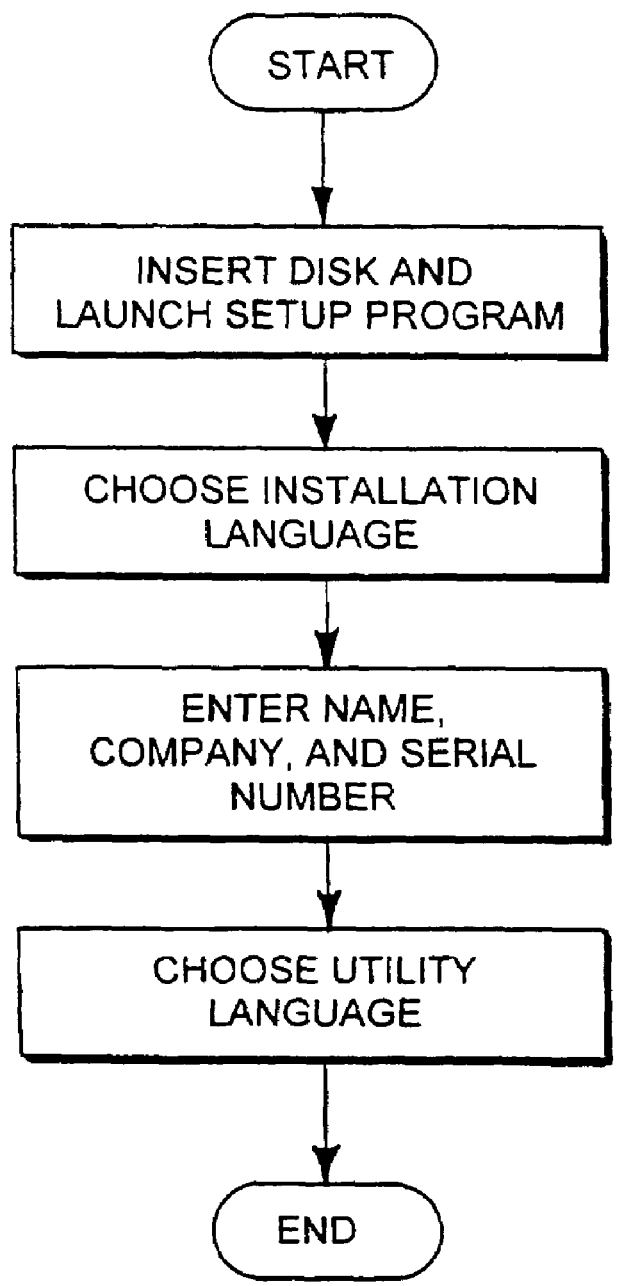
FIG. 2 illustrates installation of a utility program according to the present invention where the program is distributed on one or more disks containing the program in one or more languages; and, FIGS. 3-60 illustrate various screens displayed during the running of a utility program according to the invention.

Installation of the program 12, where the program is distributed on one or more disks containing the program in one or more languages, for example, is achieved as illustrated in FIG. 2. The user 24 may be asked to enter certain security information, for example, to verify the user 24's access to the PC 14 on which the program 12 is loaded. A program 12 screen displays a list of utility languages from which the user 24 selects one. Illustratively, the user 24 will have to reinitialize the program 12 if, after selection of a utility language, the user 24 decides to select a different utility language.

Meter Setup Manager

Certain functions of the program can be performed only while an instrument of the general type discussed above is connected through, for example, a serial cable 16 rather than through modems 20, 22 and phone line 23, to the PC 14. A Meter Setup Manager icon, for example, an illustration of the instrument 10, will appear on one of the early screens. Once the user 24 clicks on the Meter Setup Manager icon, a copyright screen will appear briefly and will be followed by a "Welcome" screen illustrated in FIG. 3. The "Welcome" screen includes a list of tasks the Meter Setup Manager is capable of performing at the user 24's option. This "Welcome" screen can be deselected at the user 24's option. If the user 24 has deselected this screen, the default task will be initialized. If the user 24 has selected the "Create a Meter Setup" option, a standard Microsoft® Windows® development tool, known as the Wizard™, is launched.

Figure 4:
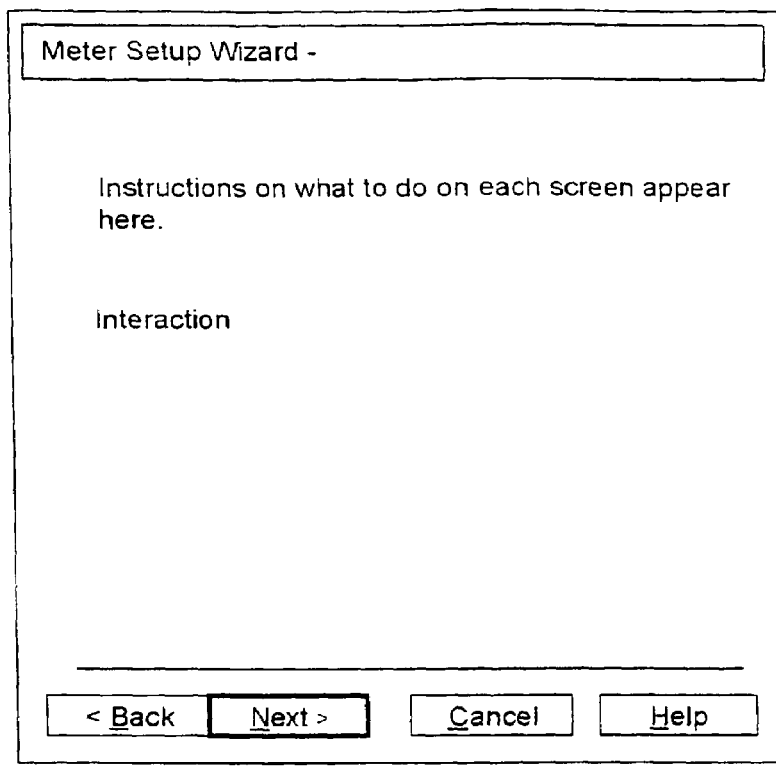
Figure 5:
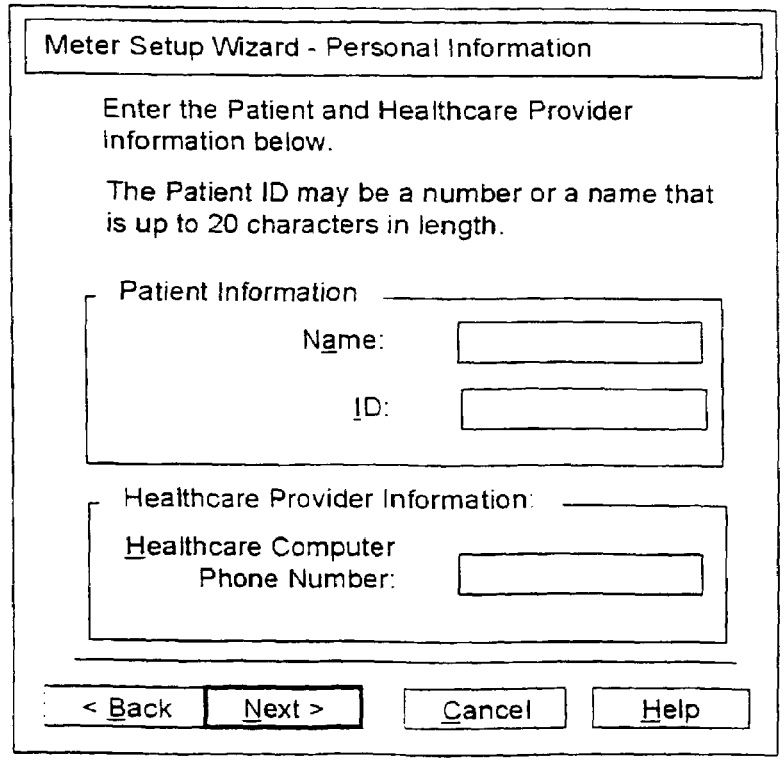

Each screen in the meter setup routine is based on the template illustrated in FIG. 4. As an example of the screens based upon this template, FIG. 5 illustrates the "Enter personal information" screen. This screen displays three fields into which the user 24 is directed to enter information pertinent to the patient whose instrument 10 is being set up. The fields are patient name, patient identification, such as, for example, patient number, patient social security number, and so on, and health care provider computer 14 phone number. The next screen, illustrated in FIG. 6, is the "Glucose units/ glucose ranges" screen. With this screen, the user 24 sets up the patient's instrument 10's glucose upper limit, glucose lower limit, hypoglycemic limit, and units of glucose measurement, for example, millimoles per liter (mmol/L) or milligrams per deciliter (mg/dL). The next screen, illustrated in FIG. 7, prompts the user 24 to set up the patient's instrument 10 for the type(s) of insulin the patient is to take, for example, REGular, NPH or 90/10, and the dosage increments, for example, tenths of a unit, half units, or whole units.

With the next screen, illustrated with sample data in FIG. 8, the user 24 is prompted to load into the patient's instrument 10 certain events which the patient is then capable of entering into the patient's diary, which the instrument 10 is equipped to keep. From a library of, for example, 255 events, fifteen are chosen from which the patient may select to enter one in his or her diary with each glucose test result. Some one or more of these may be customized for the patient whose instrument 10 is being set up.

The next screen, illustrated with sample data in FIG. 9, permits the user 24 to load into the patient's instrument 10 schedule control over any twenty-four hour period. A glucose test entry regimen dividing the twenty-four hour day into eight two-to five-hour intervals is the default regimen. This default regimen will be displayed on the screen, and the user 24 will be permitted to edit away from the default settings for the individual patient. Editing is done by clicking on the "Edit" button or by double clicking on any of the time block entries. Once the time block to be edited has been highlighted, its entries are available for edit. The program requires that every minute of the twenty-four hour period be accounted for, and does not permit any minute to be in two different time blocks. As a result, adjusting an entry will typically result in an automatic adjustment of another entry.

Advancing to the next screen, illustrated with sample data in FIG. 10, the information just entered is combined in the "Time block information" screen. The insulin types that were selected in the screen illustrated in FIG. 7 are the ones displayed on the screen illustrated in FIG. 10. If insulin type "None" was selected in connection with the setup illustrated in FIG. 7, no dosage can be selected in connection with the setup illustrated in FIG. 10. If the user 24 does not select an exercise type, he may not enter an exercise duration. The events list contains events which were selected in the events screen. The program does not permit the user 24 to list an event on the screen illustrated in FIG. 10 which was not one of the selected events in FIG. 8.

The screen illustrated in FIG. 11 is the meter setup "Insulin pump profile" screen. This screen contains a schedule list box similar to the time blocks schedule list box illustrated in FIG. 9. The user 24 selects an insulin type, and a start date and time for the insulin pump profile. The profile can contain no less than one time block and no more than twelve. The user 24 can insert or edit a time block from the screen. The user 24 can only delete a time block when the profile contains more than one time block.

Figure 12:
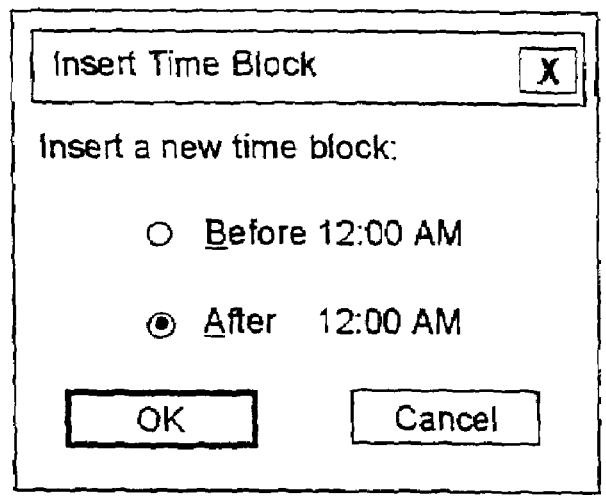

With reference to FIG. 12, the user 24 may insert a new time block by selecting a time block from the list and selecting the "Insert" button. The user 24 is presented with the option to insert the new time block either before or after the selected time block. The new time block, with a duration of one half hour, is inserted into the schedule list box. The user 24 can edit the start time of the newly added time block by double clicking on its entry in the list box, or by selecting the "Edit" button.

Figure 13:
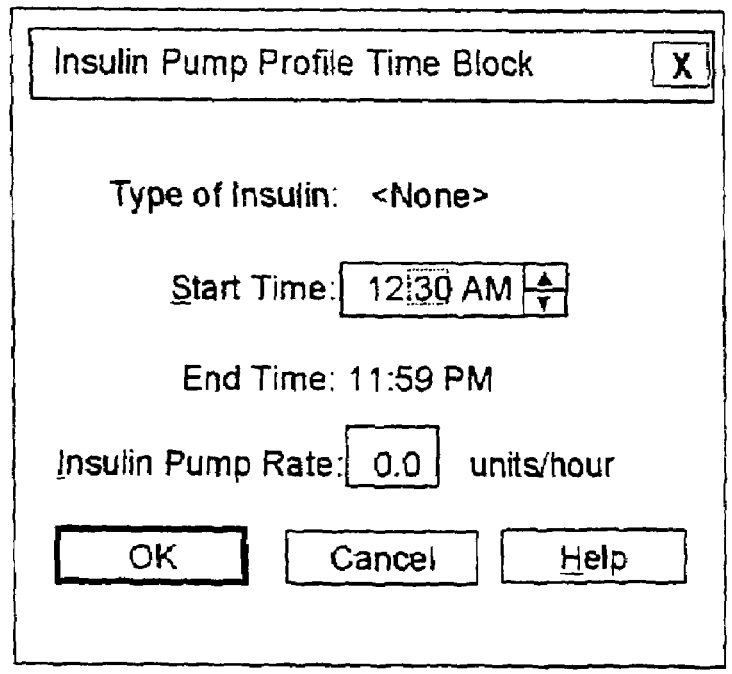

The user 24 can edit a specific insulin pump profile time block by double clicking on its entry in the profile time block list box. See FIG. 13. When this is done, the start time and insulin pump rate for the selected time block can be edited. The user 24 can also edit a time block by highlighting its entry in the time block list box and selecting the "Edit" button. All times must be part of some time block, so the user interface does not permit gaps between time blocks. Nor can time blocks overlap. Setting the start time of one block automatically adjusts the end time of the previous time block to end one minute before. The user 24 can also delete a specific profile time block by highlighting its entry in the profile list box and selecting the "Delete" button. Unless the selected time block is the first time block, the preceding time block's end time will be adjusted appropriately so that there are no gaps in the profile schedule. If the selected time block is the first time block, then the following time block's start time will be adjusted appropriately.

Referring to FIG. 14, a number of miscellaneous options relating primarily to the display of information on the instrument 10 are also user 24 selectable. For example, the format in which decimals are displayed (X.X or X,X), whether a 24 hour clock or a twelve hour one (with AM and PM), the date format (month, day, year or day, month, year), whether the instrument 10 display 28 is to be backlit or not, and whether the instrument 10's audio beeper is to be activated or not, are displayed for selection.

Figure 16:
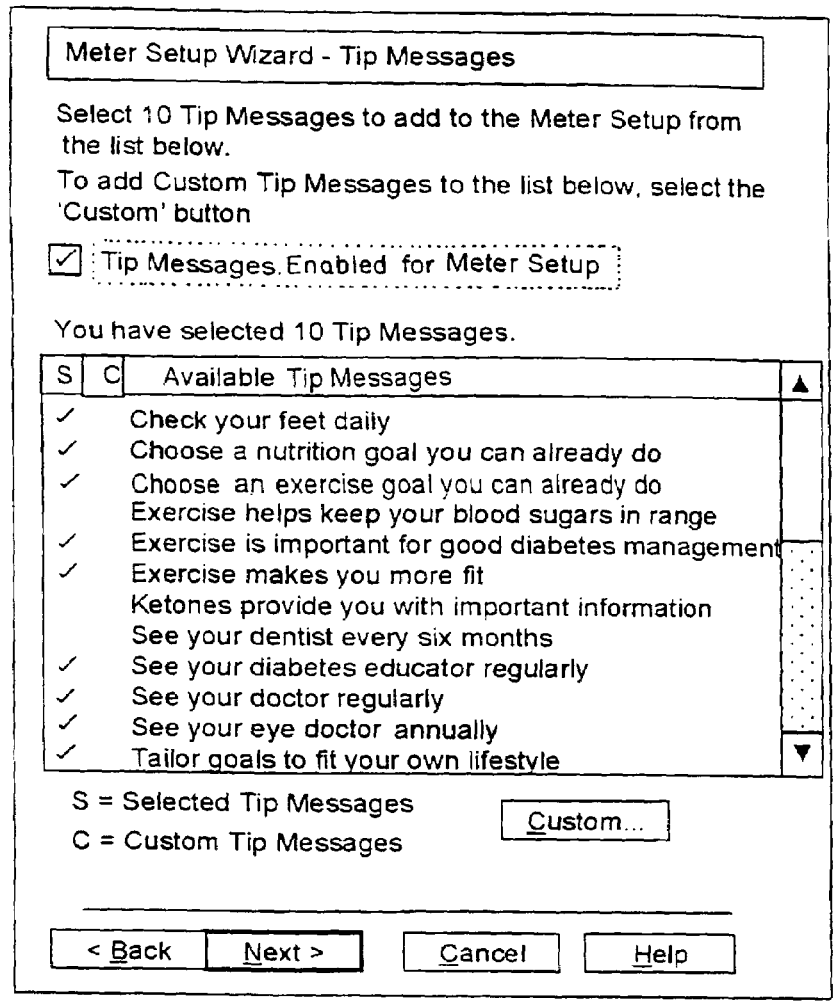

With the next screen, illustrated in FIG. 15, the user 24 selects from among a number, for example, eight, of languages in which instruments 10 can be programmed to display information, a number, for example, four, in which the particular instrument 10 being set up can display information at the patient's option. The "Tip Messages" screen, illustrated in FIG. 16, enables a list control that permits the user 24 to select a number, for example, ten, of tip messages for display on the instrument 10 being set up. If the user 24 does not want tip messages displayed on the patient's instrument 10, the user 24 may deselect the "Tip Messages Enabled for Meter Setup" box. If this box is not checked, the user 24 must select individual messages which the user 24 wants to appear on the patient's instrument 10 at appropriate times.

Figure 17:
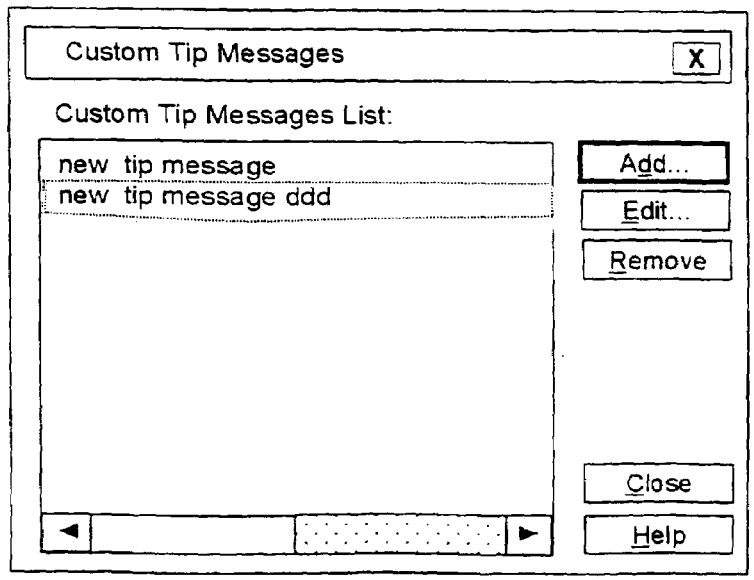
Figure 18:
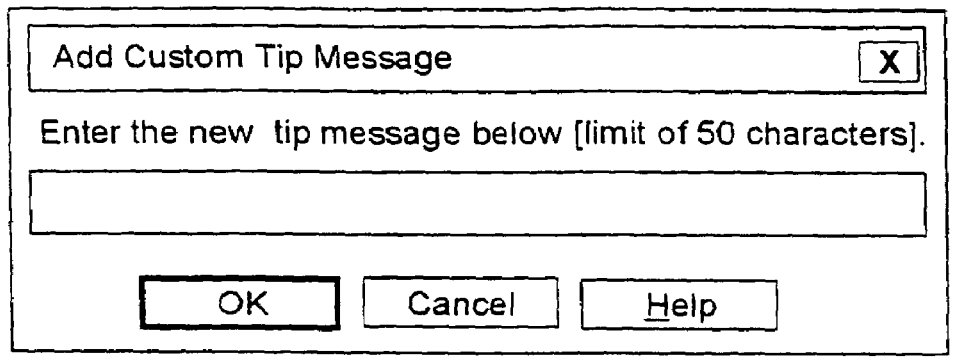
Figure 19:
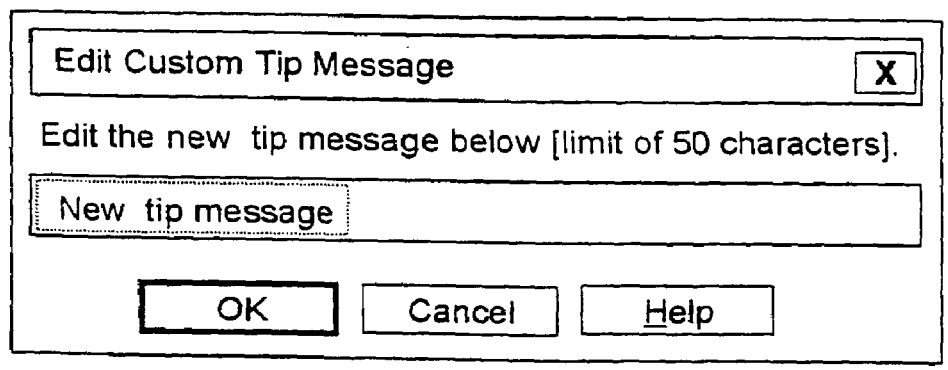
Figure 20:
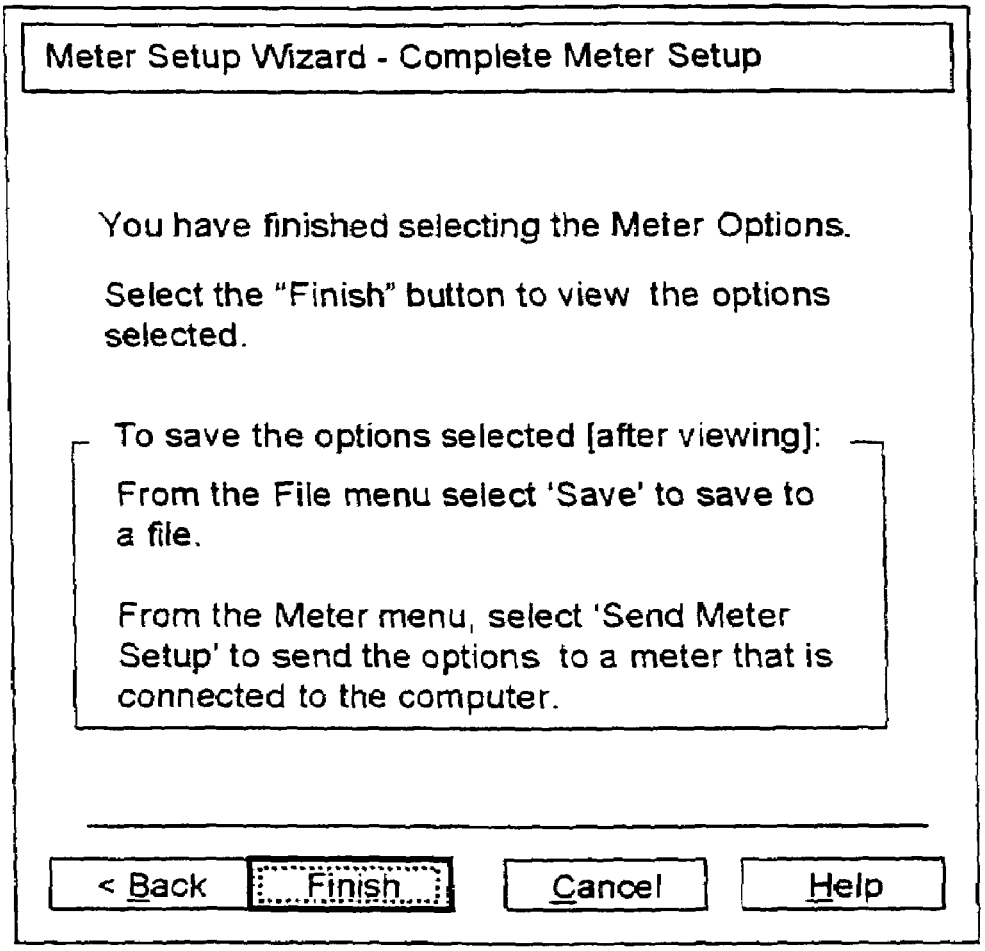

The user 24 may add custom tip messages to an instrument 10 being set up for a patient. To do this, the user 24 selects the "Custom" button. The screen illustrated in FIG. 17 is displayed. If the user 24 then selects the "Add" button, the screen illustrated in FIG. 18 is displayed. If the user 24 selects the "Edit" button, the screen illustrated in FIG. 19 is displayed. If the user 24 selects the "Remove" button, the tip message highlighted in the screen illustrated in FIG. 17 is deleted. Once these screens have been completed, the instrument 10 setup is complete. The user 24 is presented with a dialog and given instructions on how to view and save the completed setup. This screen is illustrated in FIG. 20.

Returning briefly to FIG. 3, if the user 24 selects the "Retrieve an Existing Meter Setup from a Meter" option, and no instrument 10 is connected to the PC 14, the user 24 is asked to connect the instrument 10 to the PC 14. If the user 24 selects "OK" and no instrument 10 is yet connected to the PC 14, the user 24 is again asked to connect the instrument 10 to the PC 14. If the user 24 selects "Cancel," the "Welcome" screen of FIG. 3 again appears. If the user 24 selects "Help," the help facility is launched with troubleshooting information regarding connecting an instrument 10 to the PC 14. If the user 24 selects the "Open an Existing Meter Setup File" from the "Welcome" screen, a Microsoft® Windows® file opening common dialog is launched. The user 24 may then select an instrument 10 setup file to edit or cancel back to the "Welcome" screen.

Figure 21:
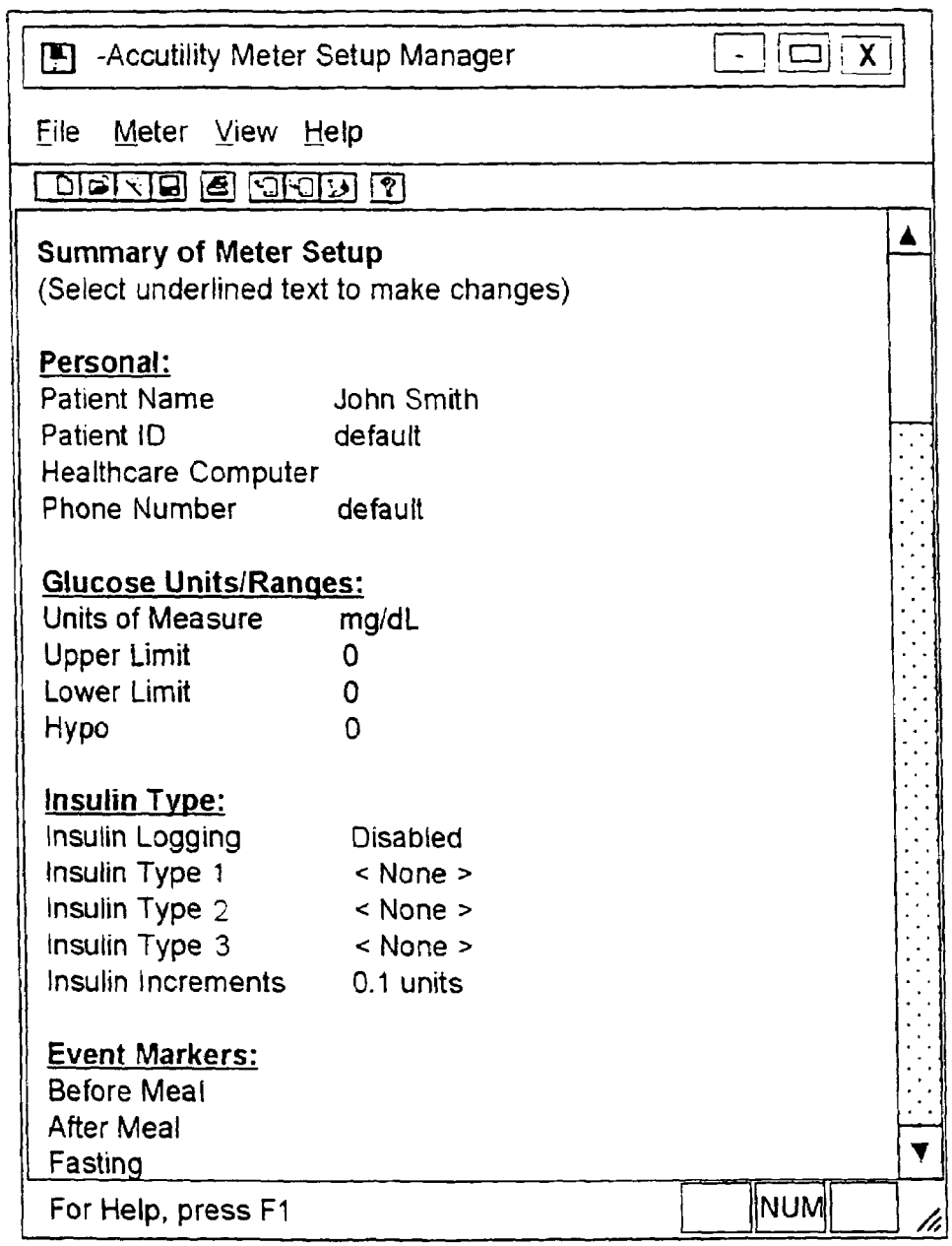

If the user 24 has selected either the "Open an Existing Meter Setup File" option or the "Retrieve an Existing Meter Setup from a Meter" option, ultimately a summary screen of the general configuration illustrated in FIG. 21 will be displayed. This screen displays the instrument 10 setup. The user 24 may edit this setup by selecting the highlighted text on the screen. The user 24 is then presented with the appropriate instrument 10 setup tab to edit instrument 10 setup options. The basic elements of the summary screen as they appear on the Microsoft® Windows® 95 platform are illustrated in FIG. 21. The title bar contains a descriptor for the data contained in the client area followed by the name of the software. This descriptor may be "New Meter," a filename, or a designation such as "John Smith's Meter." Below the title bar is a menu bar. The menu bar is described later.

Figure 22:
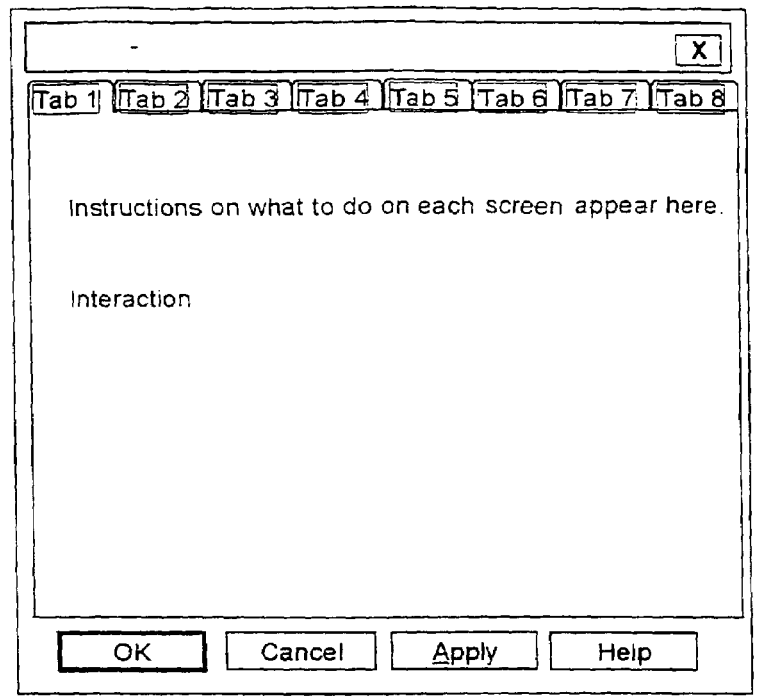

Below the menu bar, in the client area of the window, is a summary screen. This summary screen contains the current instrument 10 setup settings. The user 24 may edit the information contained on this screen by clicking on the underlined text. This activates the instrument 10 setup tabs, similarly to the screen illustrated in FIG. 22, "Instrument setup manager-tab template screen." The tab control contains screens that are nearly identical to the ones available via the instrument 10 setup Wizard™, with the difference being that the Wizard™ provides a simple, step-by-step approach to entering data, whereas the tab control gives the user 24 one-click access to any screen. The tabs can also be used to set up instruments 10. They provide a somewhat more powerful tool for doing this. However, it is suggested that, for the first few times at least, the user 24 perform instrument 10 setup using the Wizard™ as a learning tool.

Figure 23:
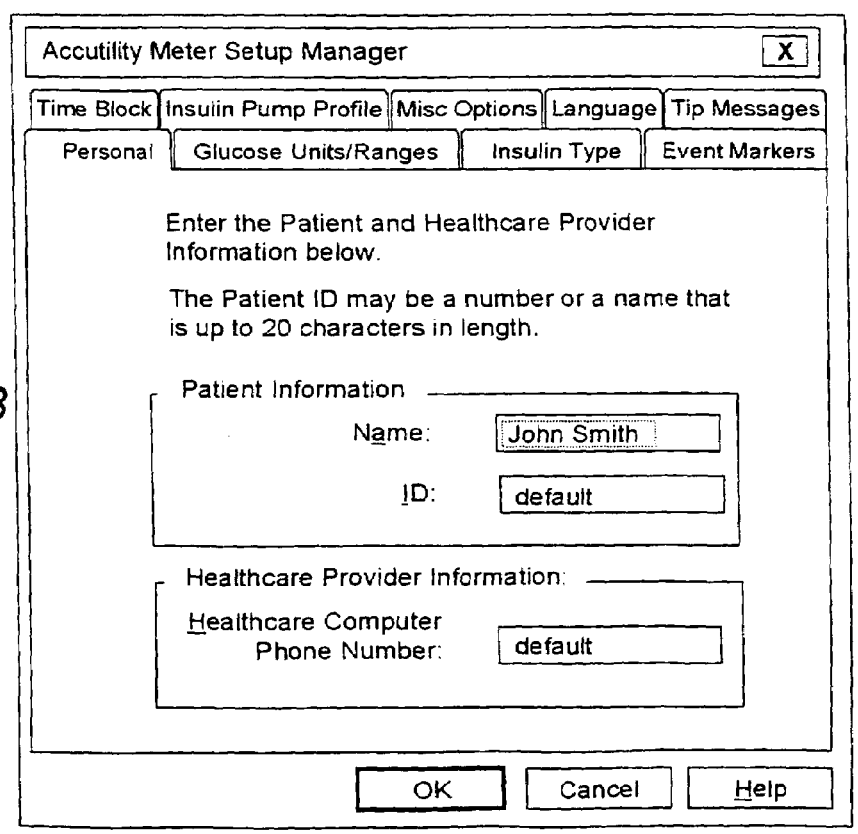
Figure 24:
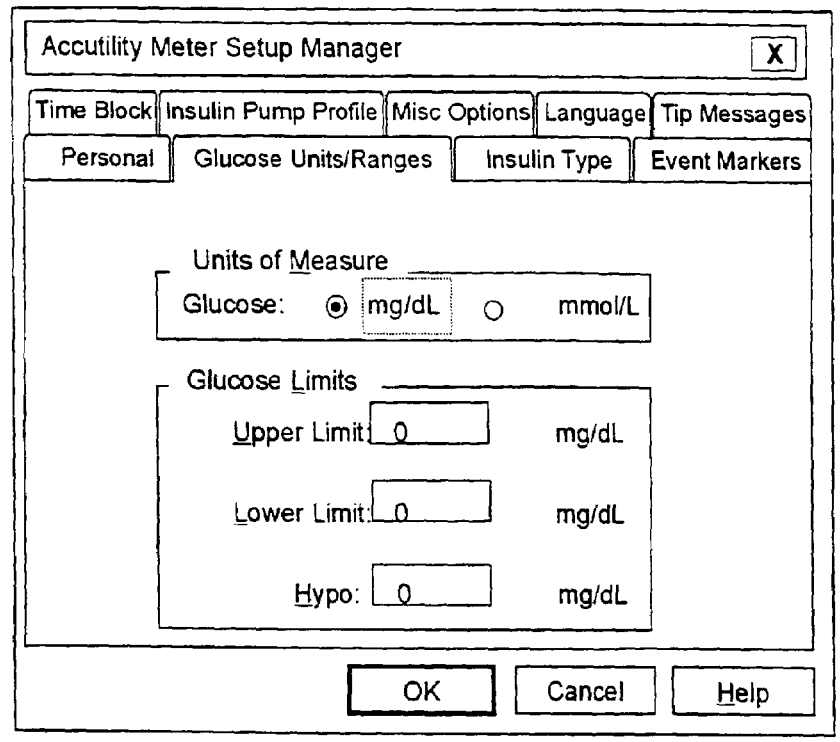
Figure 25:
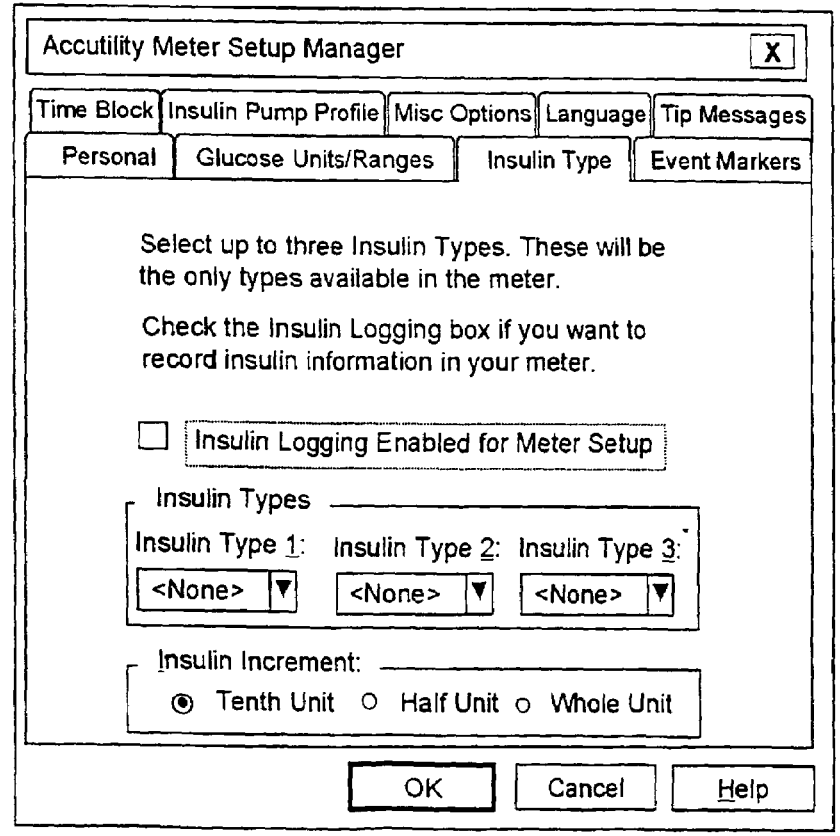
Figure 26:
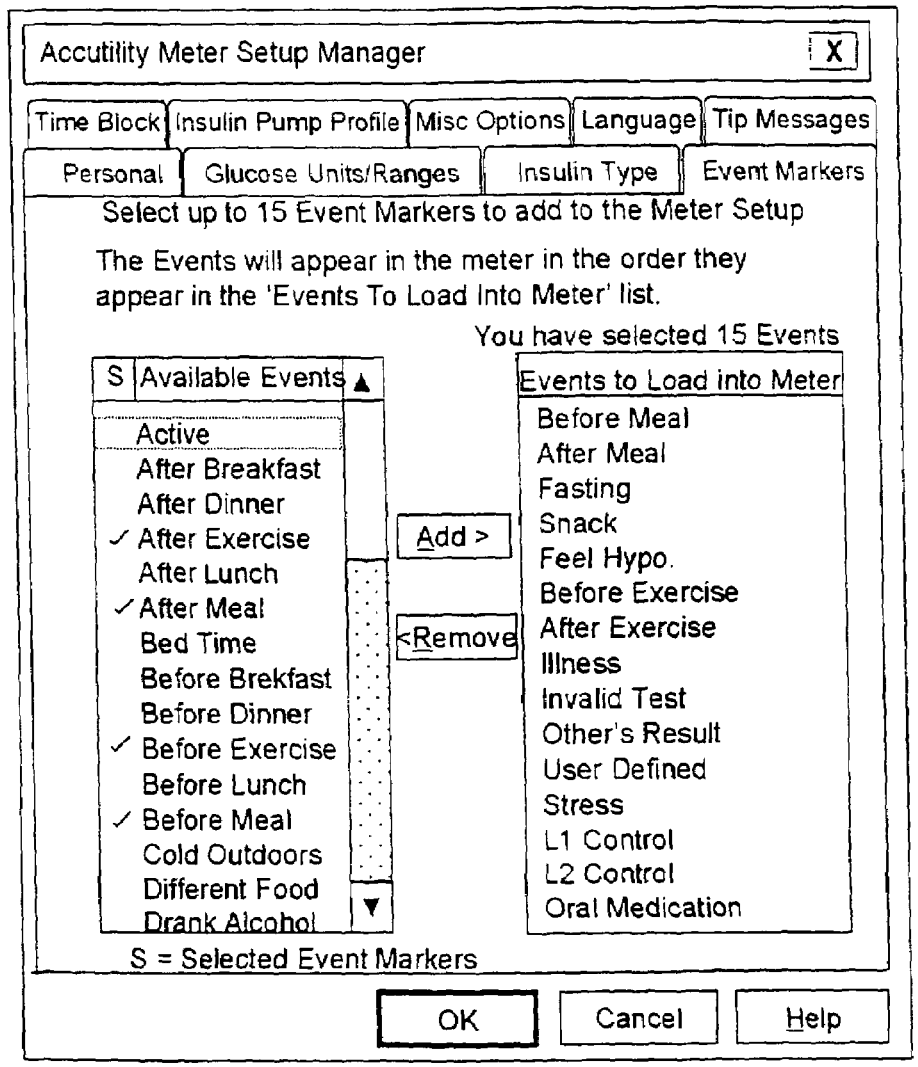

With reference to FIG. 23, the contents of the "Personal" tab are illustrated. As will be appreciated, the contents of this tab, and the appropriate user 24 interactions, are generally as described in connection with the screen illustrated in FIG. 5. Referring to FIG. 24, the contents of the "Glucose units/ranges" tab and the appropriate user interactions are generally as described in connection with the screen illustrated in FIG. 6. Turning to FIG. 25, the contents of the "Insulin type" tab are illustrated. These contents and the associated user 24 interactions are generally as described in connection with the screen illustrated in FIG. 7. Referring to FIG. 26, the contents of the "Event markers" tab and the related user 24 interactions are generally as described in connection with the screen illustrated in FIG. 8.

Figure 27:
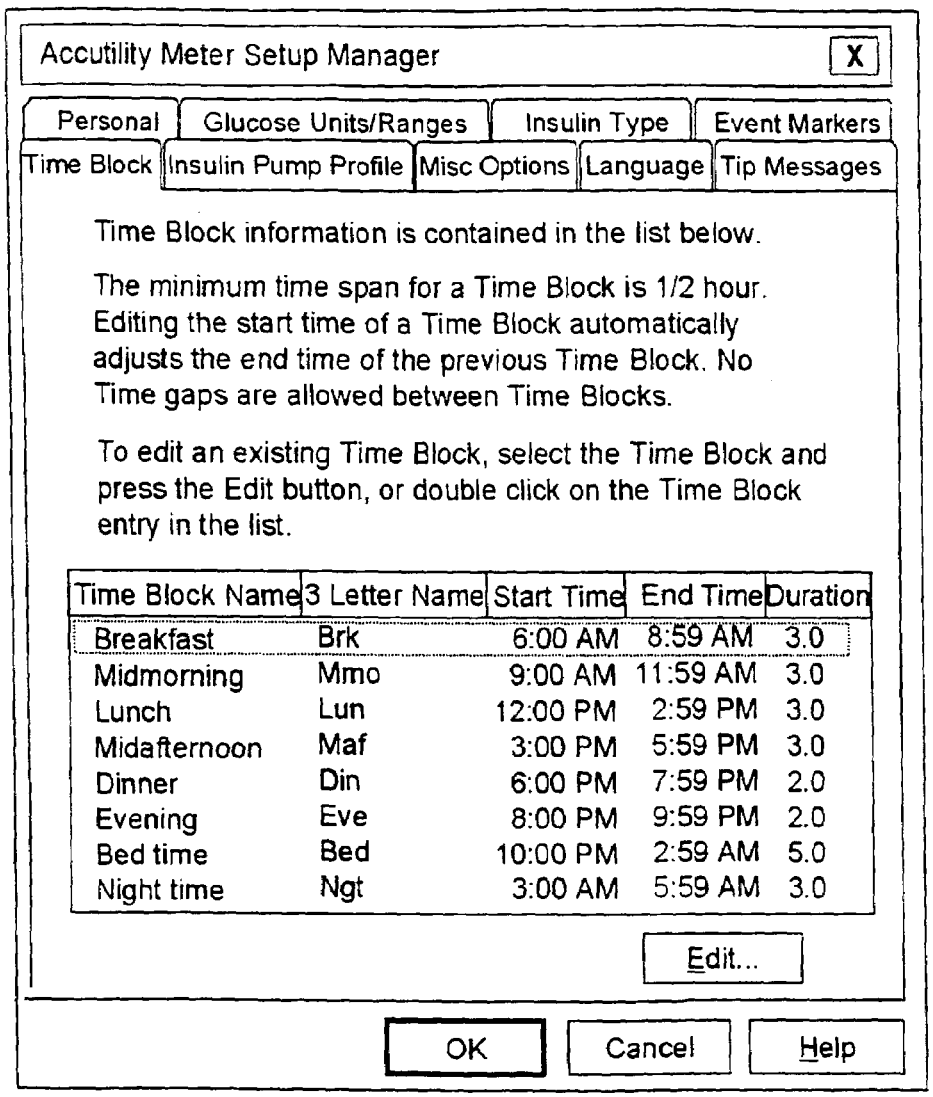
Figure 28:
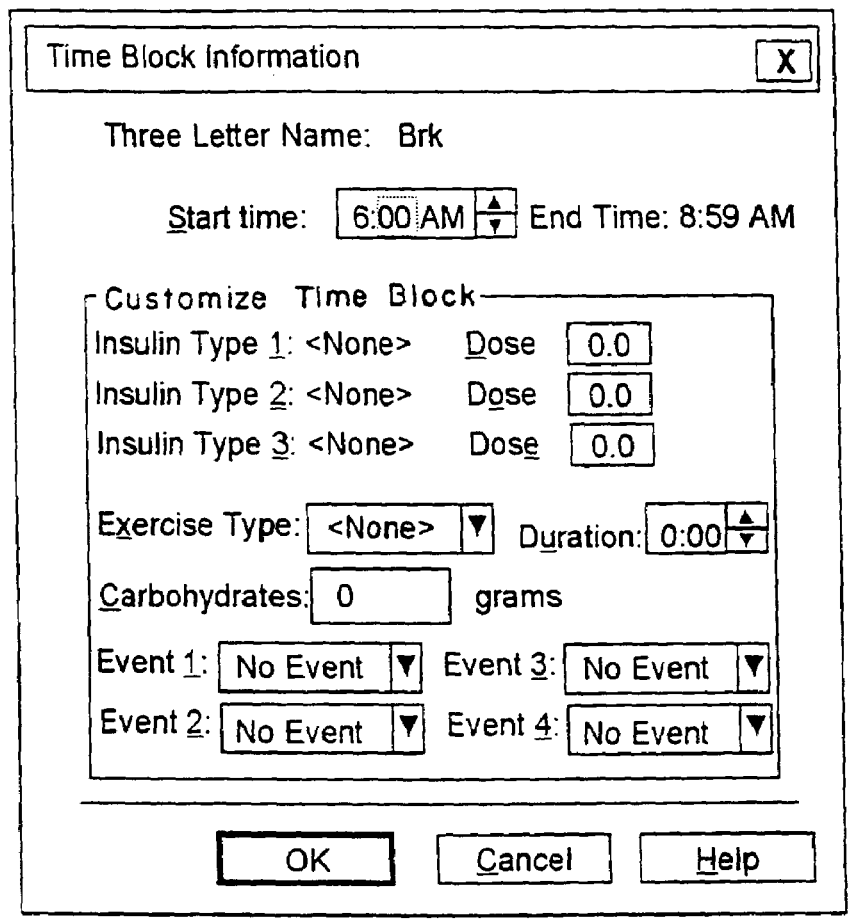
Figure 29:
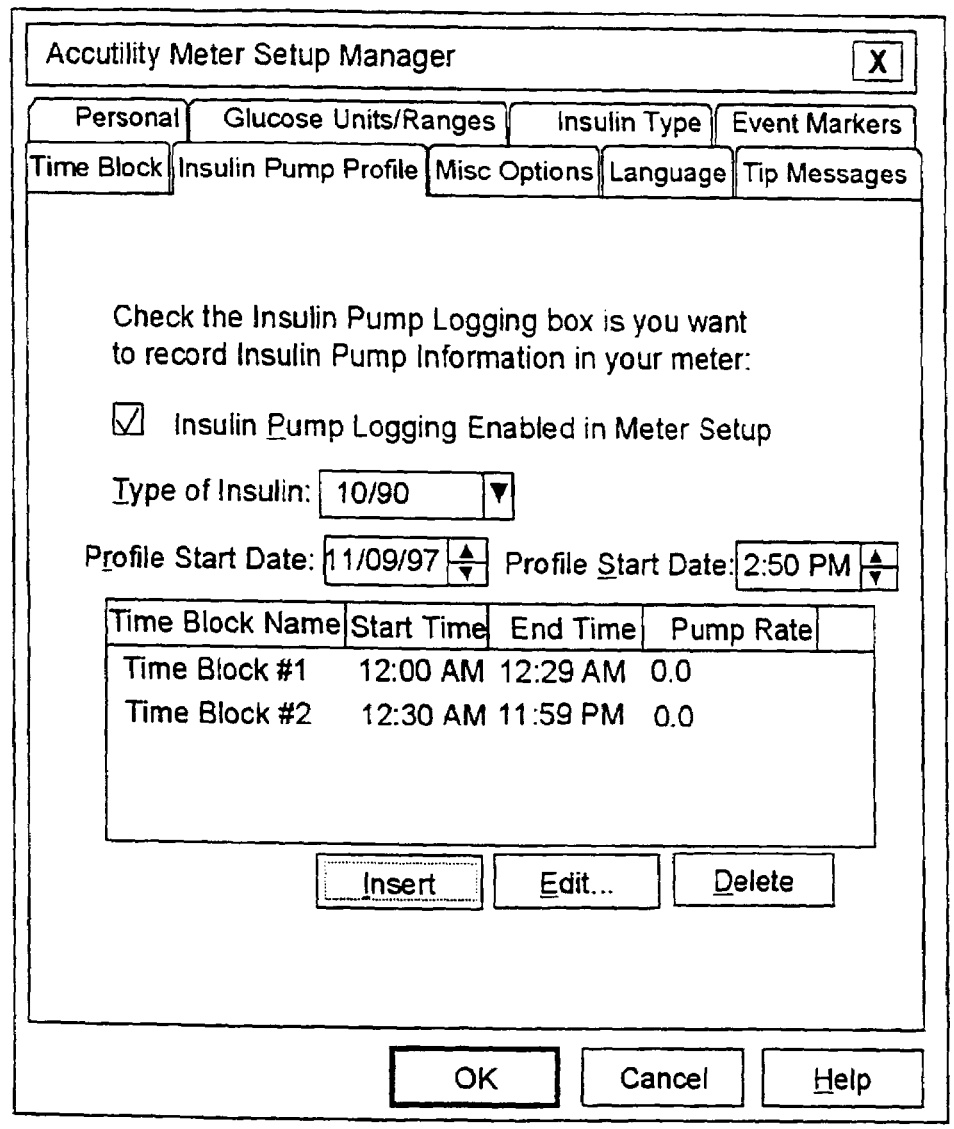
Figure 30:
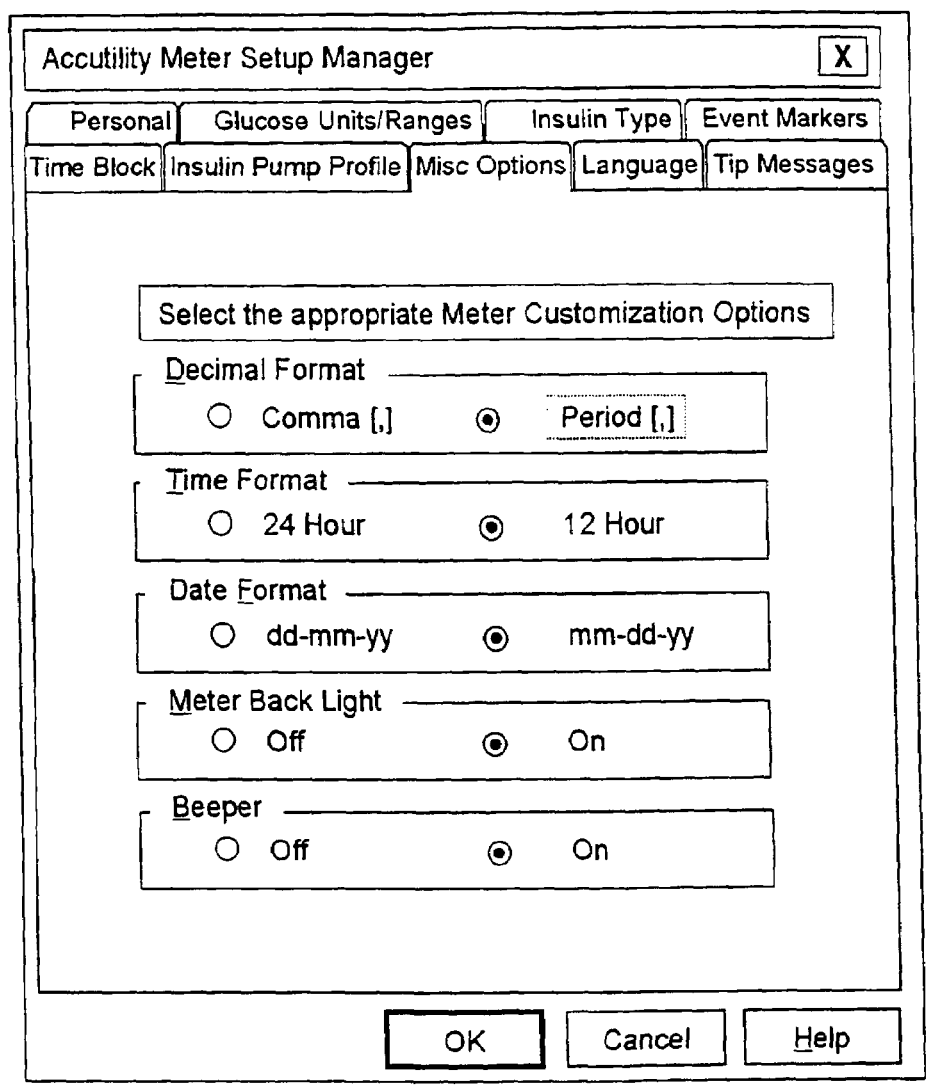
Figure 31:
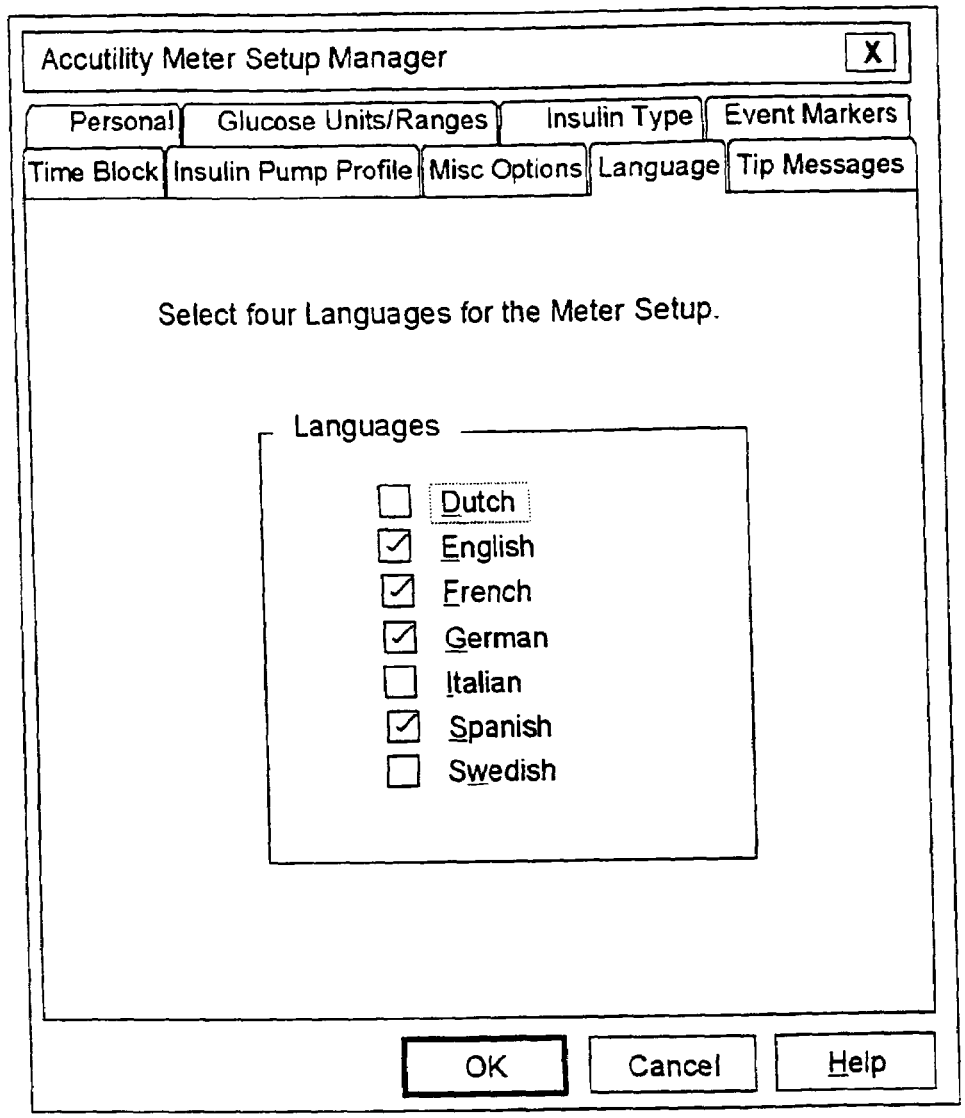
Figure 32:
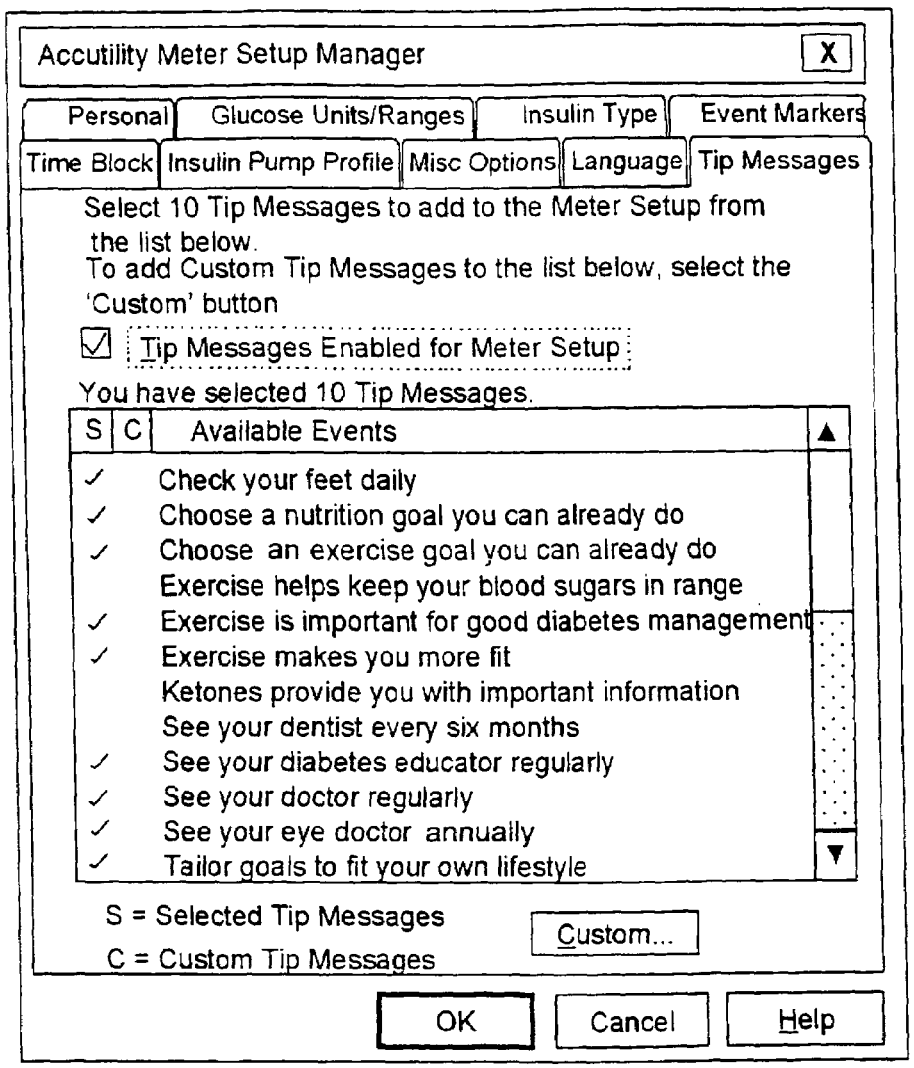

Turning to FIG. 27, the contents of the "Time blocks" tab are illustrated. These contents and the associated user 24 interactions are generally as described in connection with the screen illustrated in FIG. 9. With reference to FIG. 28, the contents of the "Time blocks" tab and user 24 interactions are generally as described in connection with the screen illustrated in FIG. 10. Referring to FIG. 29, the contents of the "insulin pump profile" tab and the related user 24 interactions are generally as described in connection with the screen illustrated in FIG. 11. Turning to FIG. 30, the contents of the "Miscellaneous options" tab and user 24 interactions associated with it are generally as described in connection with the screen illustrated in FIG. 14. With reference to FIG. 31, the contents of the "Language" tab and user 24 interactions associated with it are generally as described in connection with the screen illustrated in FIG. 15. Referring to FIG. 32, the contents of the "Tip messages" tab and user 24 interactions associated with it are generally as described in connection with the screen illustrated in FIG. 16.

Figure 3:
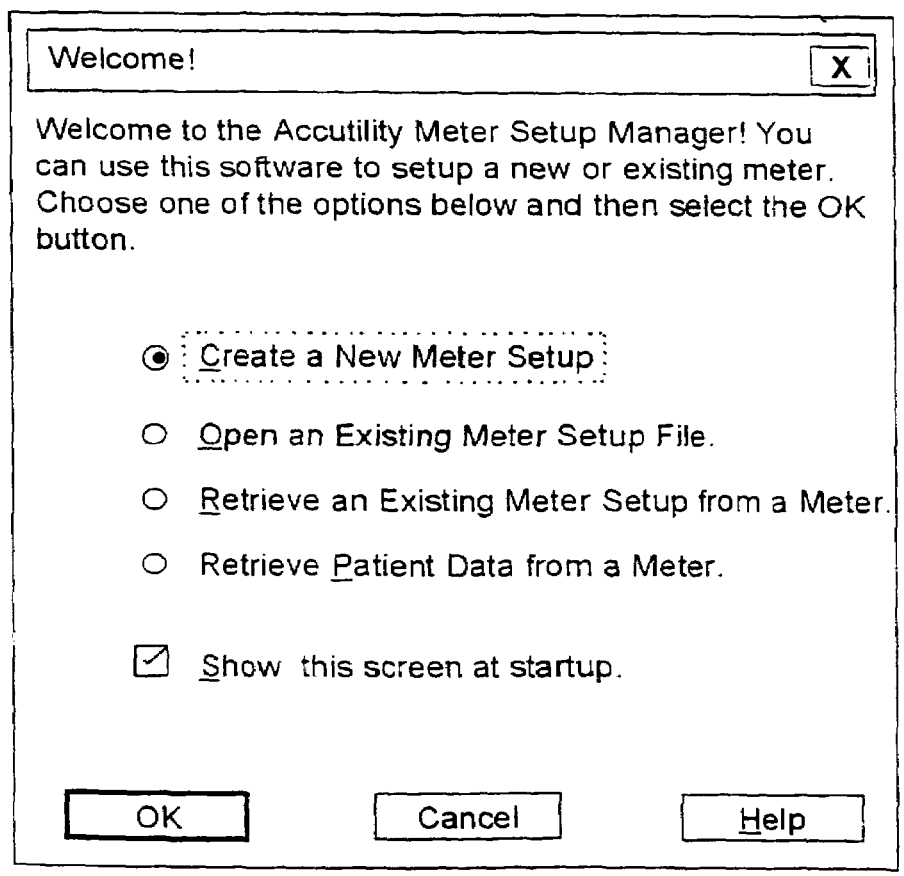

The user 24 may press a function key, F1 in the illustrated example, to open the help facility and obtain context sensitive help. All dialogs also have associated help buttons which access the help facility. The instrument 10 setup manager also has a help menu. The user 24 may cancel from the "Welcome" screen by selecting the "Cancel" button on that screen. When that action is taken, the welcome dialog box illustrated in FIG. 3 is dismissed and the main screen is displayed.

The user may select "Retrieve Patient Data from a Meter" connected to the computer 14 from the "Welcome" screen. If the user 24 then selects "OK," a sequence to retrieve patient data from a connected instrument 10 is initiated. This is exactly equivalent to selecting the "Retrieve Patient Data" option from the Meter menu. The Meter Setup Manager functions are divided into "File," "Meter," "View" and "Help" menus. See, for example, FIG. 21. The options under the "File" menu include "New," "Open . . . ," "Close," "Save," "Save As . . . ," "Print," "View Patient Report . . . ," "Print Patient Report . . . ," "Edit Patient Database . . . ," "Recent File List" and "Exit." The options under the "Meter" menu include "Retrieve Patient Data," "Retrieve Meter Setup," "Send Meter Setup," "Clear Patient Diary" and "COMmunication Port Settings . . . " The options under the "View" menu include "Toolbar," "Status Bar" and "Options . . . " The options under the "Help" menu include "Help topics" and "About . . . ."

The "File" menu contains commands that operate on Meter Setup Data and Patient Data. "New" returns all fields to their default states and initially opens a new instrument 10 setup with the Meter Setup Wizard. The user 24 may change this setting to Meter Setup Tabs by selecting "Options" under the "View" menu. If there is any unsaved data in the fields, the user 24 is prompted to save it. "Open" prompts the user 24 to name a file to open and opens a Meter Setup File. If the selected file is not an instrument 10 setup file, an error message is displayed and the Summary Screen is blank. If the selected file is an instrument 10 setup file, then the data is initially displayed with the Summary Screen. The user 24 may edit the open document with the Meter Setup Tabs by clicking on the underlined text, or may edit the open document with the Meter Setup Wizard™ by selecting the Wizard™ toolbar button.

Figure 33:
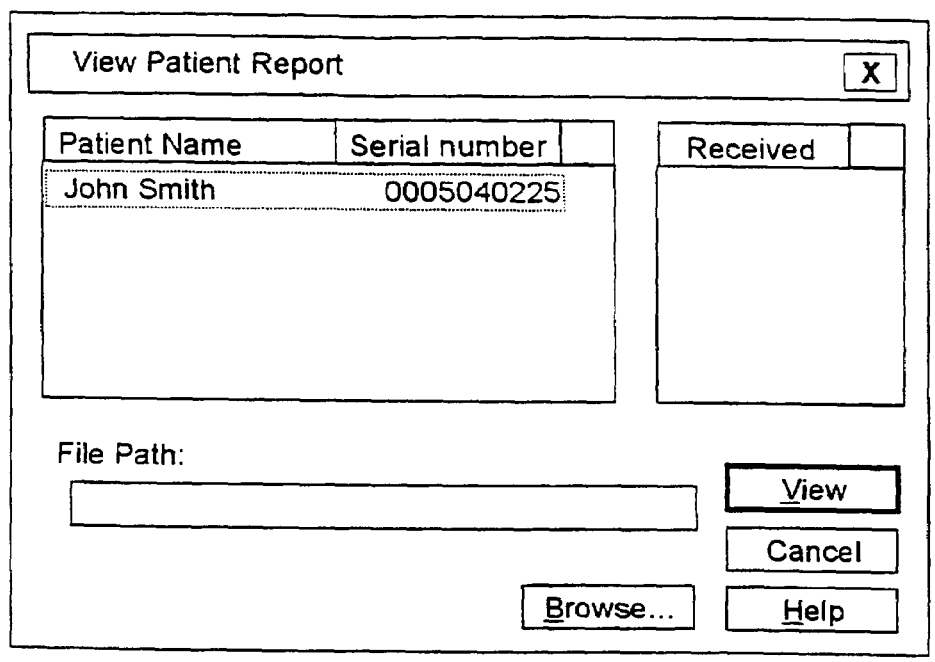
Figure 34:
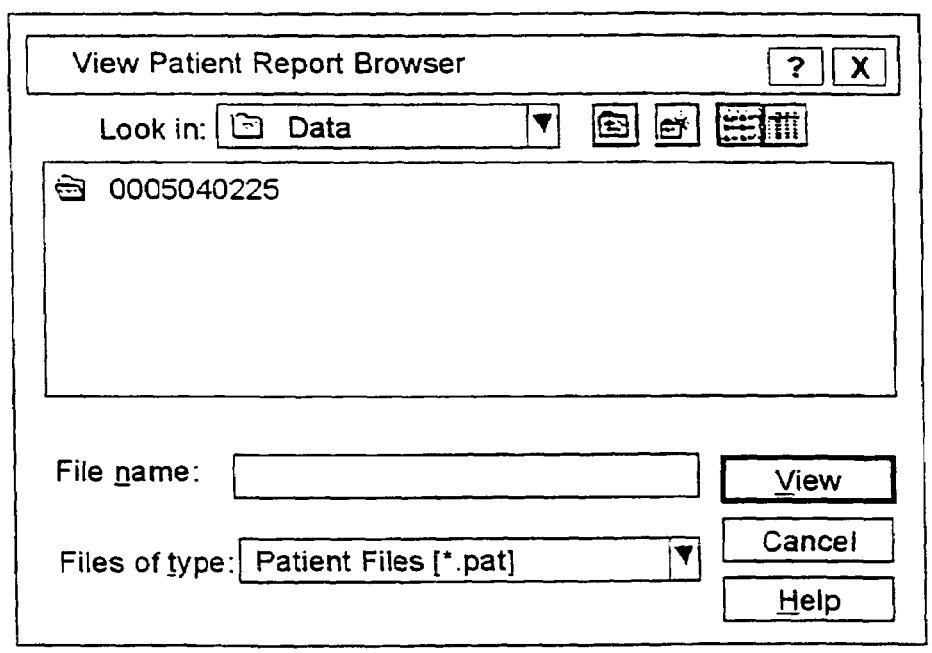
Figure 36:
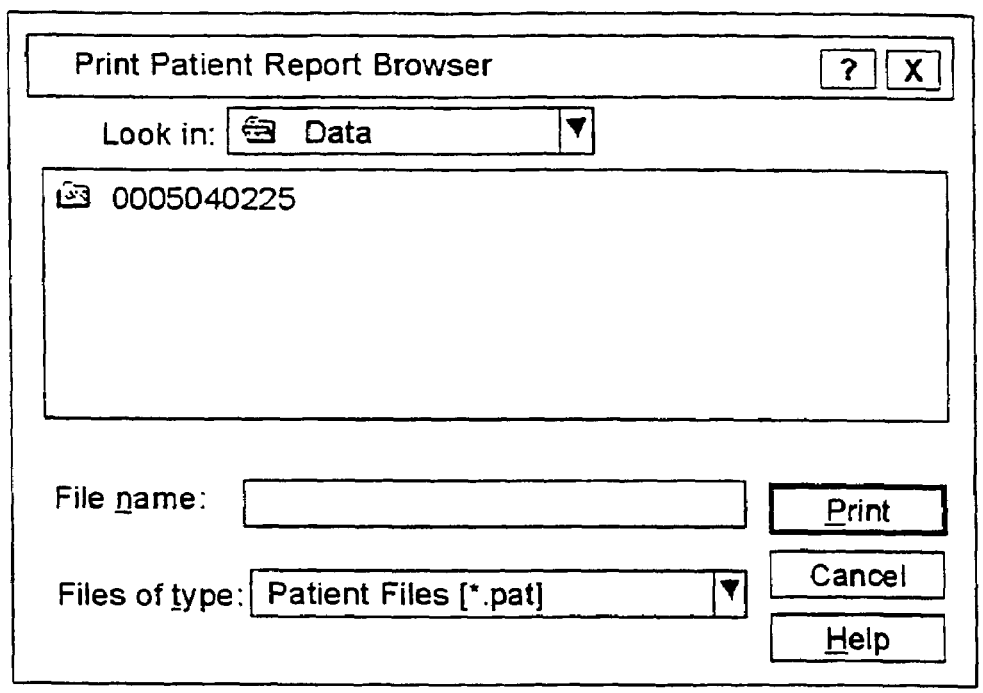
Figure 37:
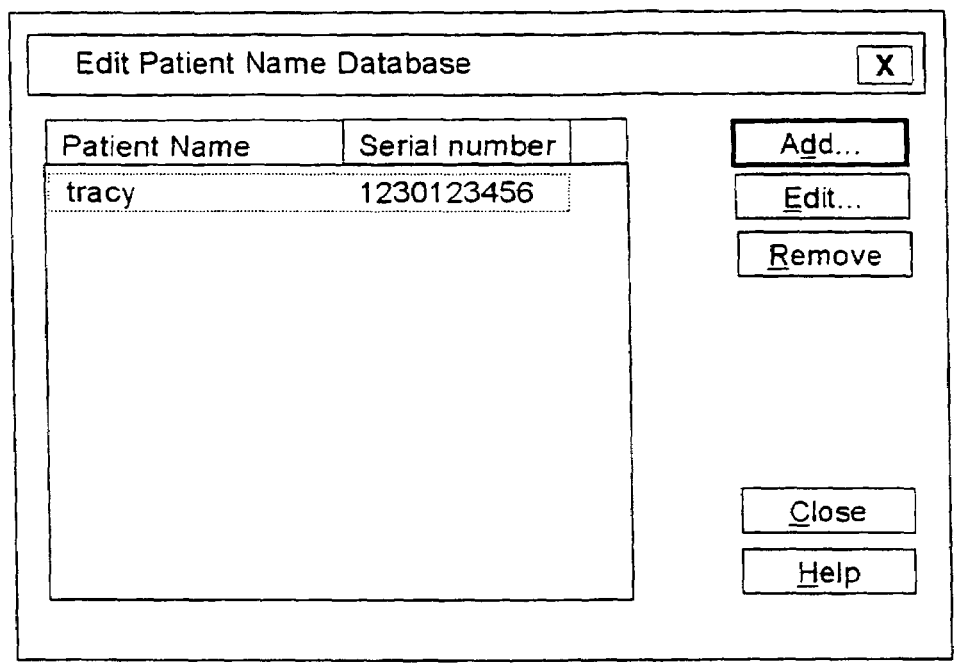
Figure 38:
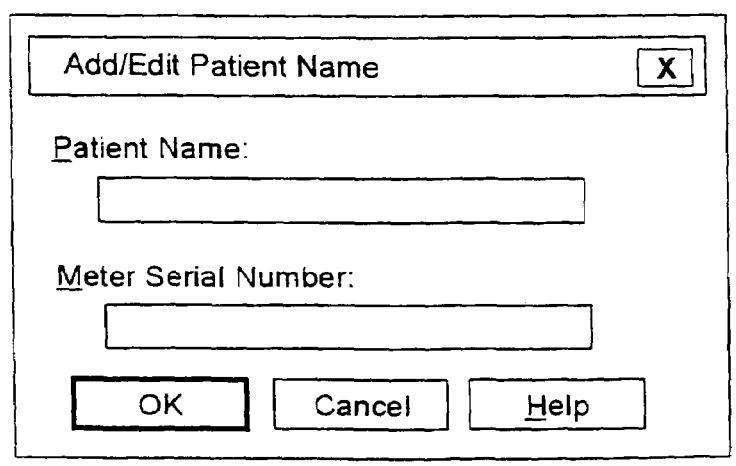

"Close" closes the currently open instrument 10 setup file. If the currently open instrument 10 setup file has not been saved, the user 24 will be prompted to save it. "Save" saves the currently open file. If the file has not yet been assigned a name, the user 24 will be prompted to assign it a name and location. "Save As" saves the current file under the assigned name. The user 24 is prompted to assign it a name and location. "Print" prints the current instrument 10 setup data. "View Patient Report . . . " prompts the user 24 to identify a patient data file to view using the patient name, instrument 10 serial number and the date received or the actual file name to select the file for viewing. "View Patient Report . . . " causes the selected report to be displayed in the format specified by the user 24. See FIG. 33. The user 24 selects the report format by selecting "Options" from the "View" menu. "View Patient Report Browser," FIG. 34, is accessed by the user 24 clicking on the "Browse . . . . " button on the screen illustrated in FIG. 33. "View Patient Report Browser" permits the user 24 to scroll through the patient reports saved in the database for one the user wishes to view. "Print Patient Report . . . " causes the selected report to be printed. The user 24 selects the report to be printed in response to a prompt from this routine. See FIG. 35. "Print Patient Report Browser," FIG. 36, is accessed by the user 24 clicking on the "Browse . . . " button on the screen illustrated in FIG. 35. "Print Patient Report Browser" permits the user 24 to scroll through the patient reports saved in the database for one the user 24 wishes to print. "Edit Patient Database . . . " permits the user 24 to add, delete and edit patient name-to-instrument 10 serial number associations. See FIGS. 37 and 38. "Recent File List" causes the four most recently opened files form the Patient Data and Meter Setup databases to be displayed, and permits the user 24 to open one of these files by selecting it from the list. "Exit" causes the computer 14 to exit from the Meter Setup Manager routine.

Figure 39:
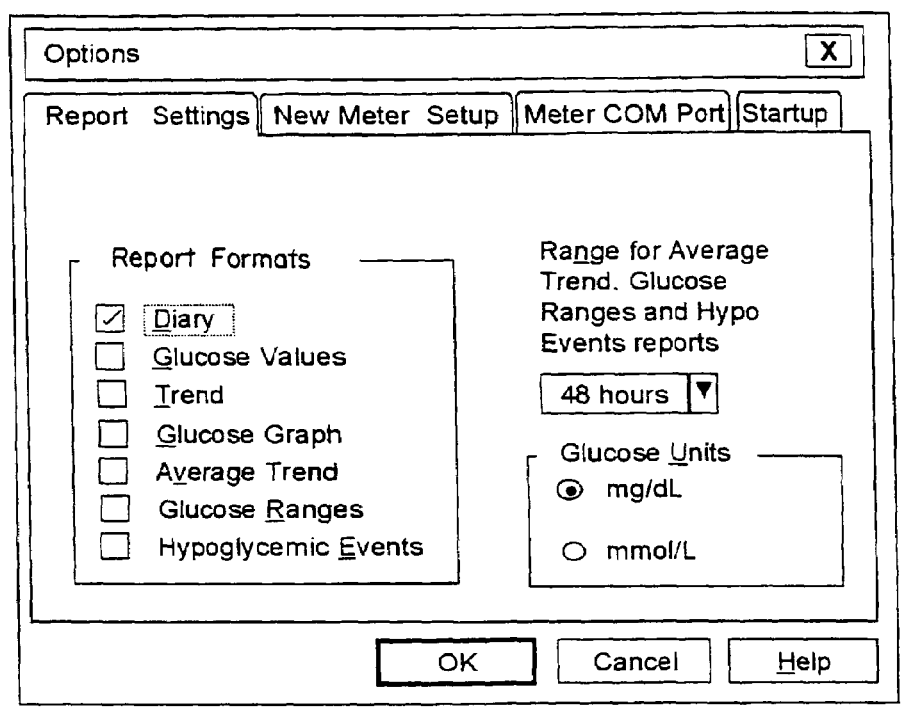
Figure 40:
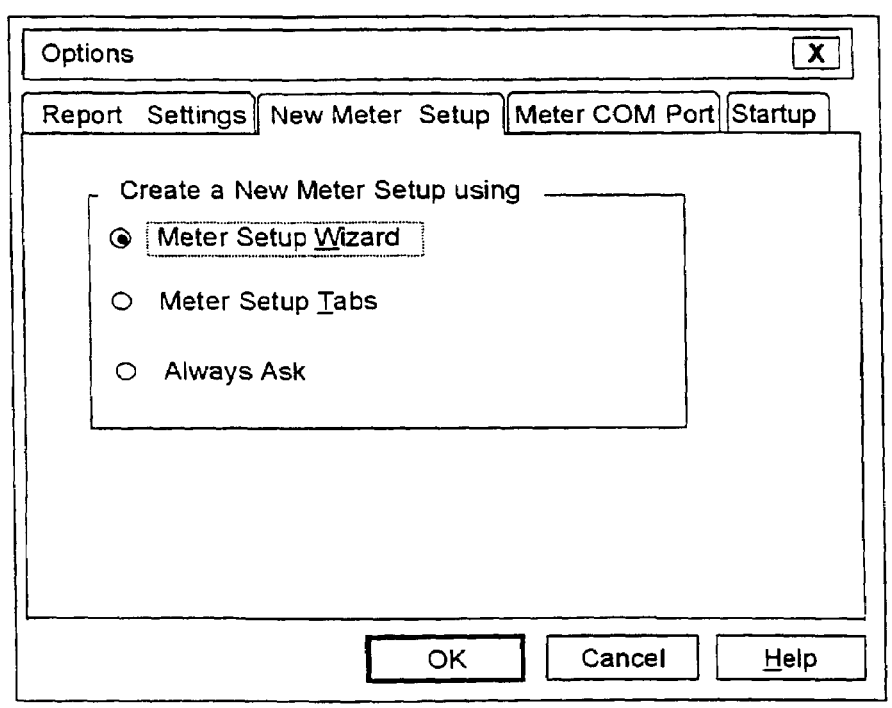
Figure 41:
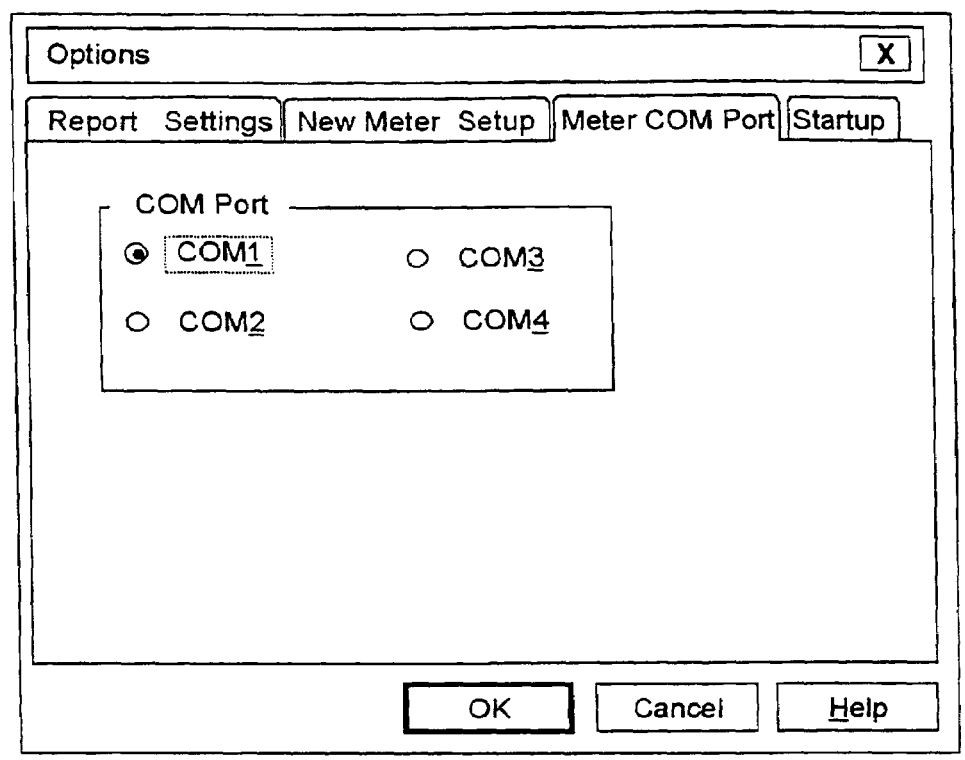
Figure 42:
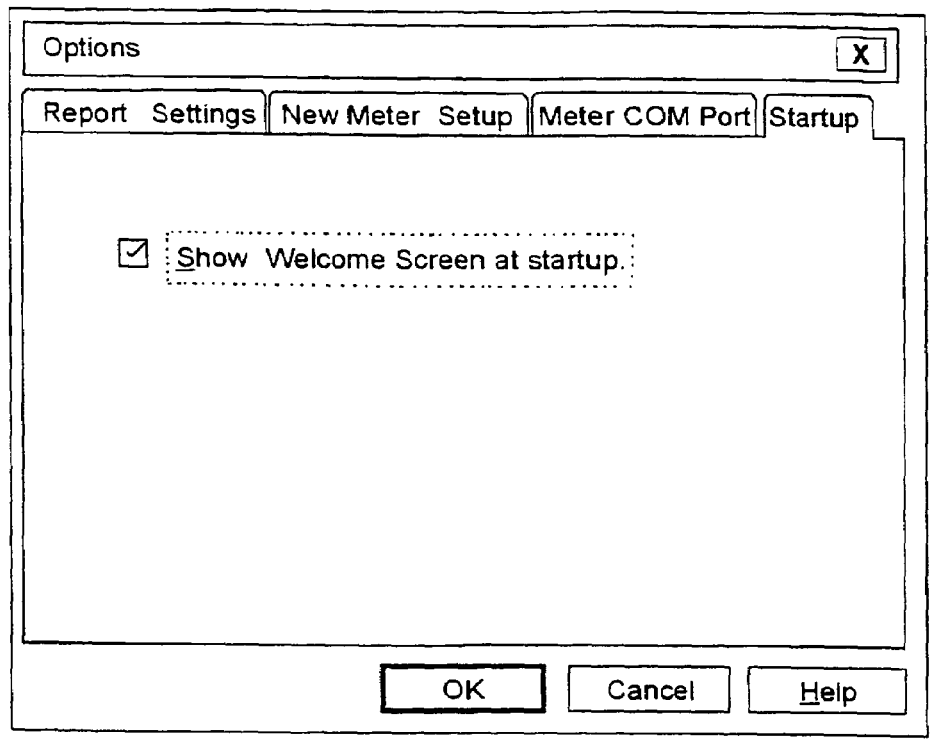

The "Meter" menu contains commands that act upon the instrument 10 that is connected to the computer 14. "Retrieve Patient Data" prompts the user 24 to enter a filename and a location to save the patient data to, and then retrieves the patient data from the instrument 10 connected to the computer 14. If no instrument 10 is connected to the computer 14, the user 24 is prompted to connect one. Once the data transfer is complete, the patient data is displayed in the format selected by the user 24. An "Options" screen illustrated in FIG. 39 permits the user 24 to select various Meter Setup Manager application options. For example, under the "Report settings" tab, the user 24 is prompted to select from among the various report formats: "Diary," "Glucose values," Trend," "Glucose graph," "Average trend," Glucose ranges," and "Hypoglycemic events." The user 24 is also prompted to select the time range for average trend, glucose ranges and hypoglycemic events reports. The user 24 is further prompted to select the glucose units, for example, mg/dL or mmol/L, for the reports. Under the "New meter setup" tab, the user 24 is prompted to select how new instrument 10 setup will be performed, permitting the user 24 to select the Meter Setup Wizard™, or use the tabs, or instructing the Meter Setup Manager always to ask how instrument 10 setup is to be performed. See FIG. 40 and the discussion of FIG. 22 above. Under the "Meter COM port" tab, the user 24 is prompted to select the computer 14 port 18 through which communication with the instrument 10 will be conducted. See FIG. 41. Referring to FIG. 42, under the "Startup" tab, the user 24 is prompted to indicate whether the "Welcome" screen, FIG. 3, should be displayed at startup.

Figure 43:
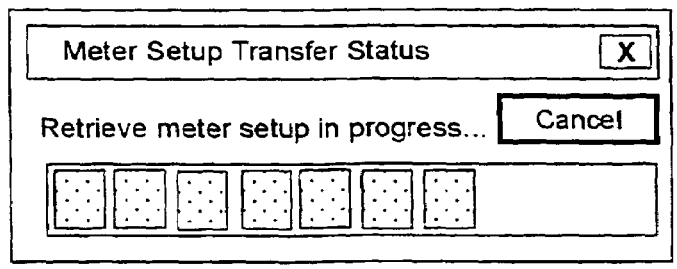
Figure 44:
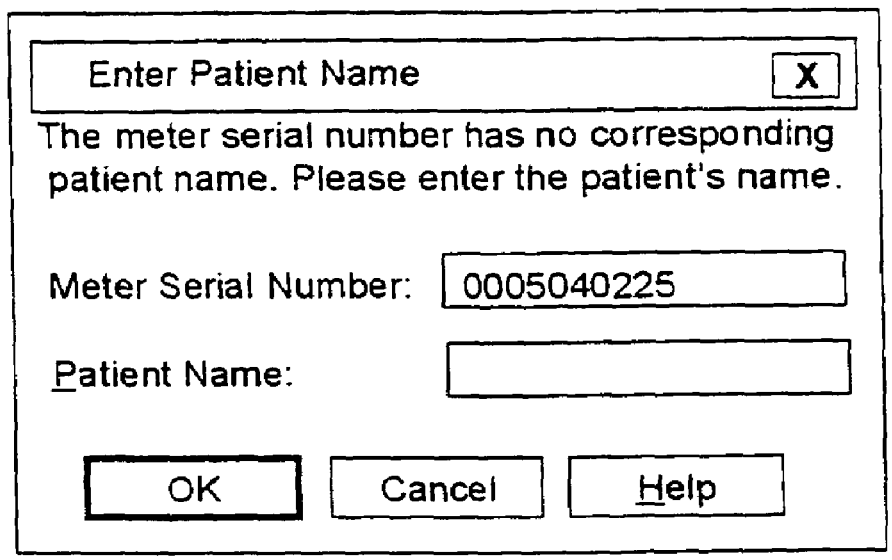

"Retrieve Meter Setup" retrieves the Meter Setup Data from an instrument 10 and displays the instrument 10 setup data using the Summary Screen. If no instrument 10 is connected to the computer 14, the user 24 is prompted to connect one. FIG. 43 illustrates the screen which is displayed when instrument 10 setup status data is being transferred. When the instrument 10 setup data transfer is complete, if the instrument 10 serial number does not have associated with it a patient name, the "Enter Patient Name" prompt appears, FIG. 44, prompting the user 24 to enter the patient's name. The entered patient's name then appears on the summary screen.

Figure 45:
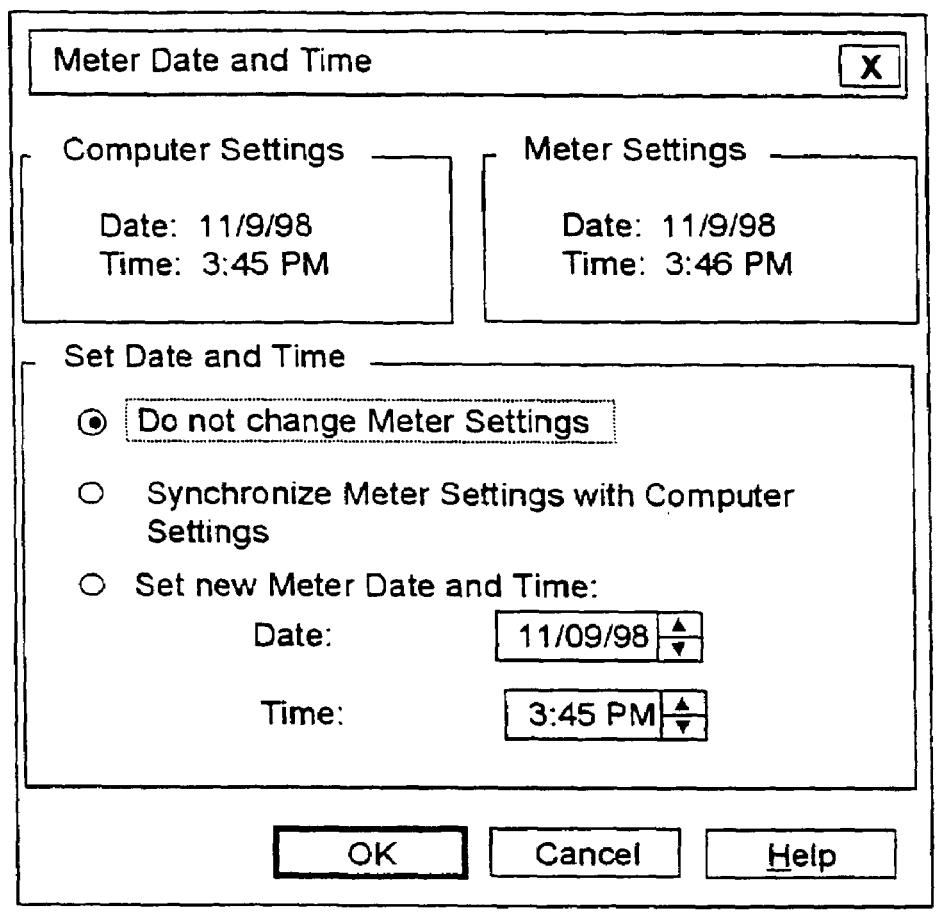
Figure 46:
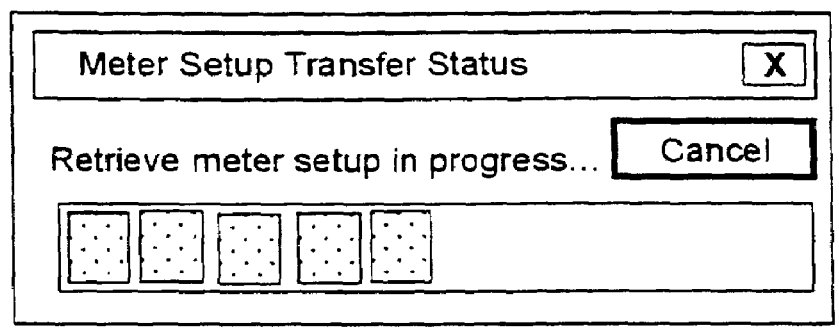

"Send Meter Setup" sends instrument 10 setup data to an instrument 10 connected to the computer 14. If no instrument 10 is connected to the computer 14, the user 24 will be prompted to connect one. Before the instrument 10 setup data is sent to the instrument 10, the user 24 is prompted to set the date and time on the instrument 10. The user 24 has the option of not changing the instrument 10's date and time, synchronizing the instrument 10's date and time to the computer 14's or manually setting the instrument 10's date and time. See FIG. 45. As the instrument 10 setup data is being sent to the instrument 10, the screen illustrated in FIG. 46 is displayed.

Figure 47:
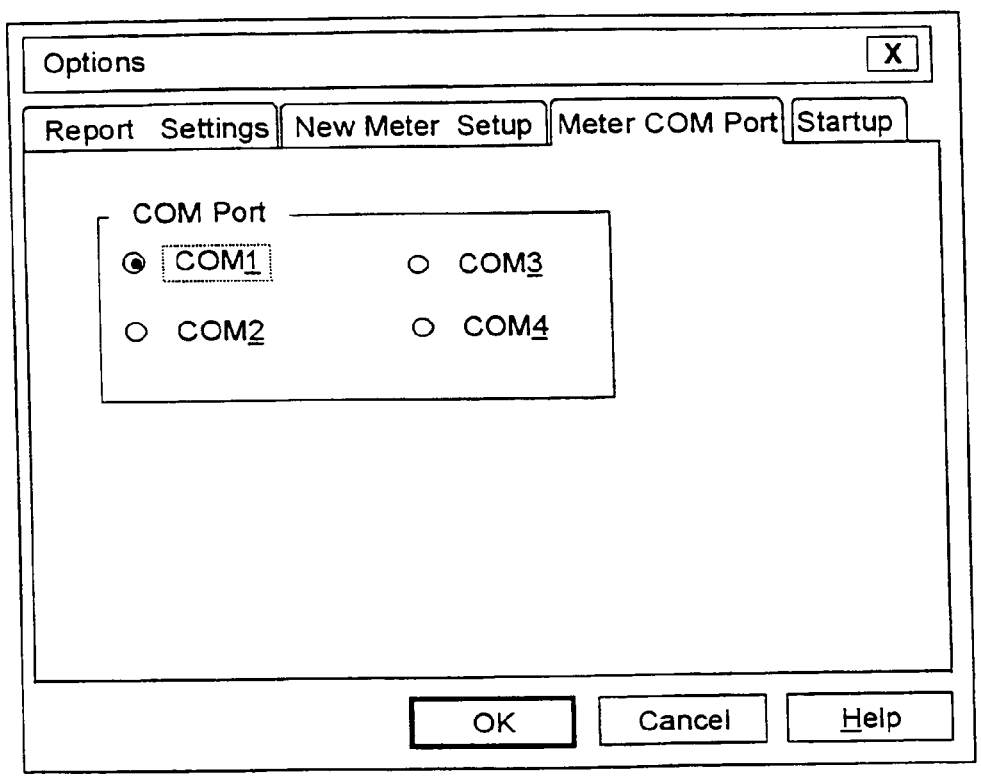
Figure 48:
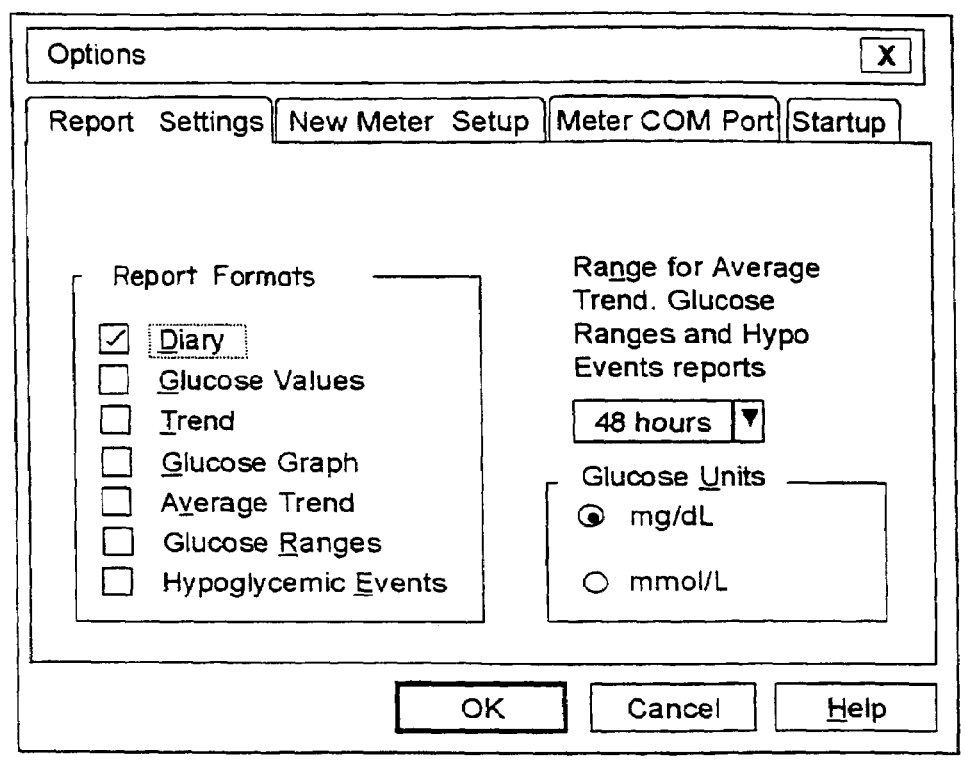
Figure 49:
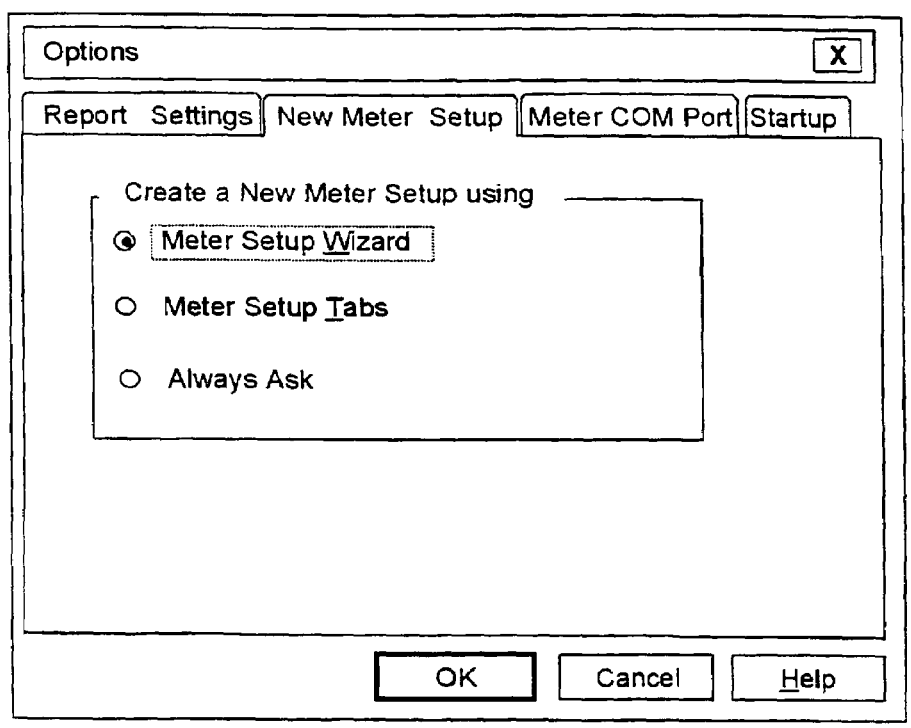
Figure 50:
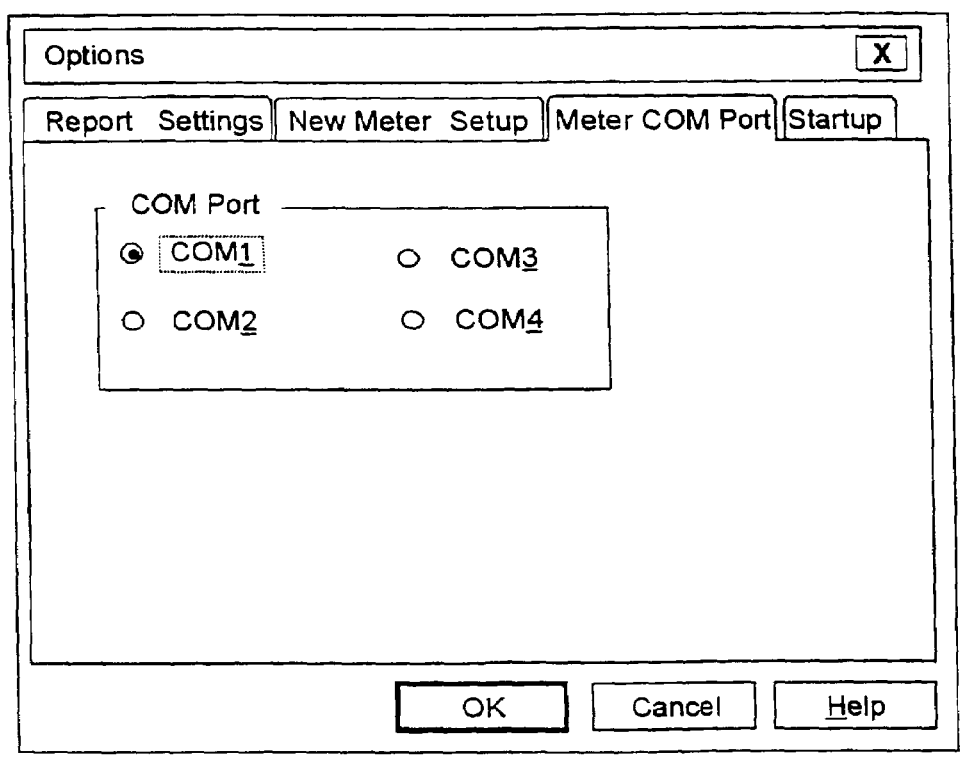
Figure 51:
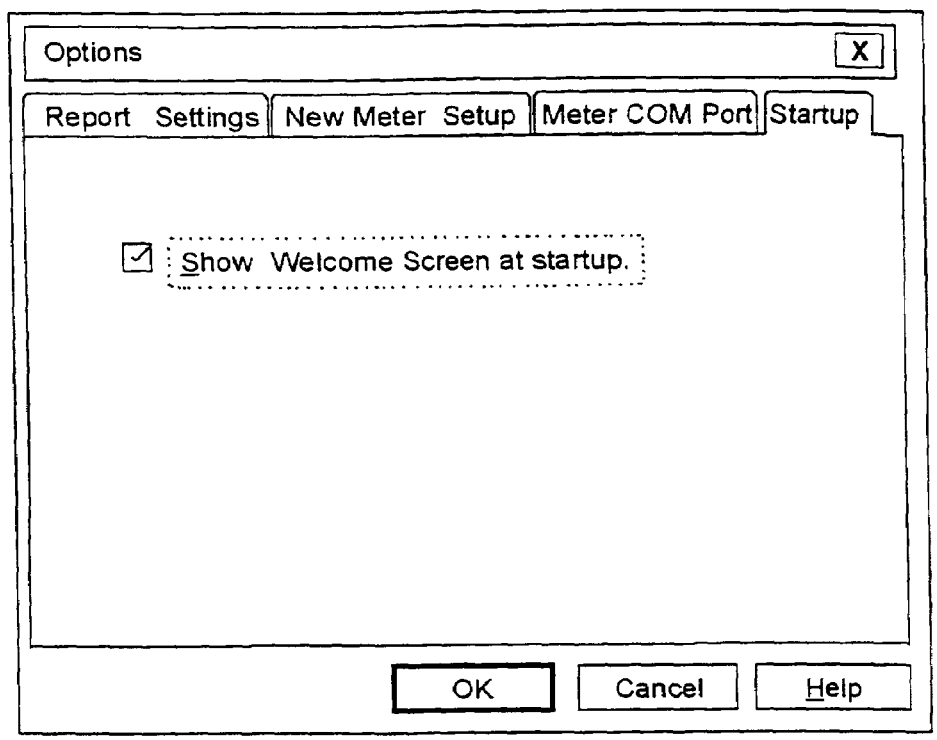

"Clear Patient Diary" clears the patient diary data of an instrument 10 connected to the computer 14. To prevent accidental clearing of diary, the user 24 is prompted to save patient data to files before proceeding with clearing of patient diary from an instrument 10. If no instrument 10 is connected to the computer 14, the user 24 will be prompted to connect one. "COM Port Settings" causes the screen illustrated in FIG. 47 to be displayed. The user 24 is prompted to select the computer 14 port 18 through which communication with the instrument 10 will be conducted.

The "View" menu contains items that adjust the settings for the Meter Setup Manager. The "Toolbar" command permits the user 24 to select whether the toolbar is displayed. The "Status Bar" command permits the user 24 to select whether the status bar, which is located at the bottom of the Meter Setup Manager application screen, is displayed. "Options" creates a display which permits the user 24 to choose various Meter Setup Manager application options. This multi-page display is illustrated in FIGS. 48-51. See the above discussion of FIGS. 39-42.

The "Help" menu contains items that provide the user 24 with access to information about the Meter Setup Manager. "Help Topics" displays the table of contents of a help file. The user 24 may navigate via hyperlinks from the table of contents to the contents of the various help file entries. The "About" entry causes the version of the software and copyright notice information to be displayed.

The toolbar for the Meter Setup Manager contains command buttons for commonly accessed features, such as "File-New," "File-Open," "File-Save," "File-Print," "Meter Setup Wizard," "Meter Communication-Retrieve Meter Setup," "Meter Communication-Send Meter Setup" and "Meter Communication-Retrieve Patient Data."

Phone-In Manager

All functions related to telephone modem 20, 22-based communication between a patient's instrument 10' and the user 24's computer 14 fall within the control of the Phone-In Manager routine. Consequently, the Phone-In Manager routine illustratively runs all of the time. Installation of the utility program 12 places a link to the Phone-In Manager routine's executable in the Microsoft® Windows® startup folder, so that the Phone-In Manager routine launches automatically whenever Microsoft® Windows® launches. In rare cases, the user 24 may need to launch the Phone-In Manager routine by double clicking on its icon, for example, an illustration of a telephone, or by other Microsoft® Windows® convention.

After the Phone-In Manager routine is launched, a copyright screen will appear briefly. After launch, Phone-In Manager is generally minimized. This waiting state is generally referred to herein as "Wait for New Calls." The user 24 may also "Review Calls" or "Perform Administrative Tasks." From the perspective of a patient who is using an instrument 10', the patient's data may be sent to the health care professional's office prior to a scheduled appointment. The patient may also phone the patient data in to the health care professional's office at any time, as necessary, to permit the health care professional to review it. From the perspective of the health care professional, such a connection is completely automatic. The patient performs all necessary interactions to achieve the data transfer.

Figure 52:
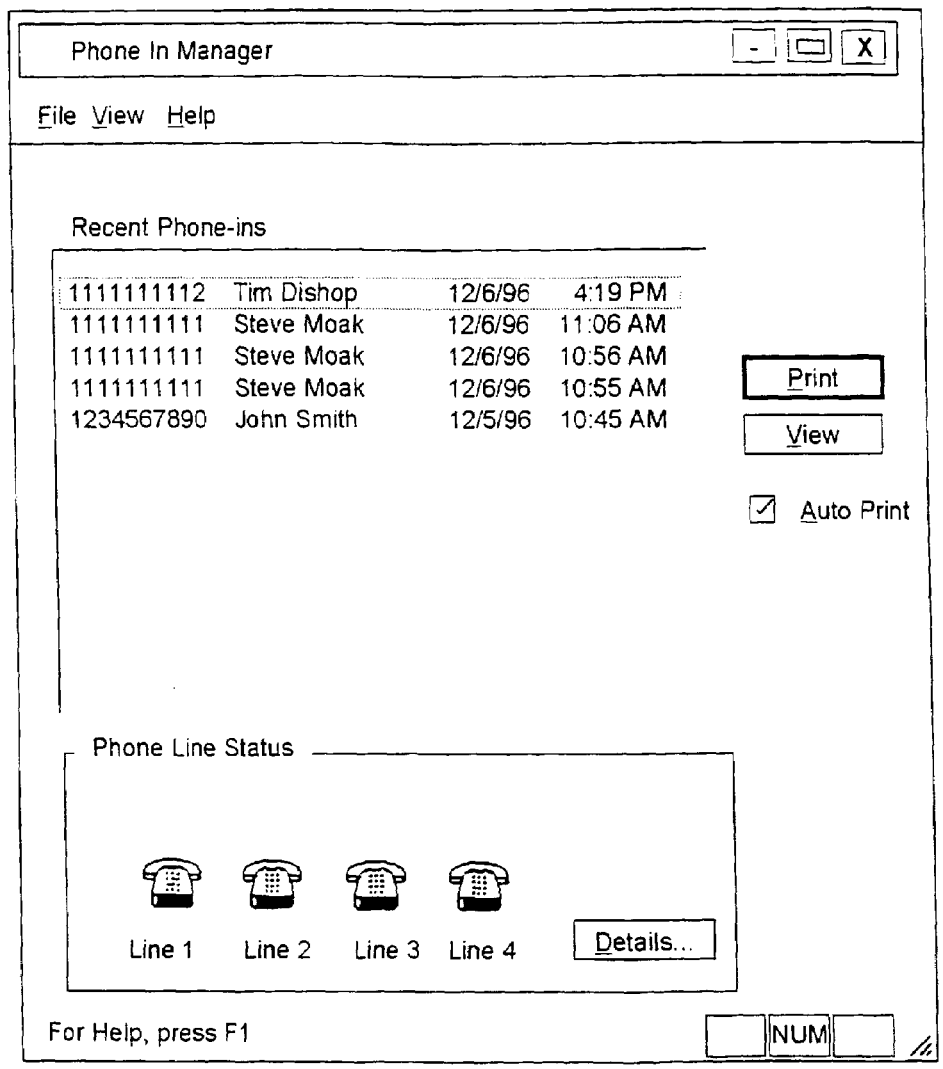

As previously noted, Phone-In Manager is always running, at least as a background task. It will be active only when a phone call comes in to the health care professional's office computer 14 or when a user 24 restores it to display status on the computer 14 monitor. A user 24 restores Phone-In Manager, for example, to review calls or to change any of the Phone-In Manager configuration options. FIG. 52 illustrates the Phone-In Manager main screen restored. When patients phone their data in via modems 20, 22 to the health care professional's computer 14, the Phone-In Manager keeps track of each call and the data that was received.

All calls are logged in order from most recent to oldest. Each logged call is displayed in the list with the instrument 10' serial number, patient's name if available, and the time and date of the phone call. The user 24 of the computer 14 may view or print patient data by highlighting the desired patient's instrument 10' serial number and selecting the "View" or "Print" button, respectively. The user 24 may also select the "Auto Print" option, in which case incoming patient data is automatically printed. The user 24 may also view or print patient data which has expired from the Recent Calls list displayed in the screen illustrated in FIG. 52. Selecting the "View" button results in the display of the selected patient's data in the format illustrated in FIG. 53. The user 24 can then choose to print or close this file. The user 24 can also view this screen by selecting old files to view from the menu. The files can be selected by the serial number of the instrument 10', patient name and data transfer date, or by file name. Selecting the "Print" button results in the printing of the selected patient's data in the report format illustrated in FIG. 53. The user 24 can also print files which have expired from the Recent Calls list by selecting old files to print from the menu. Again, the files to be printed can be selected by the serial number of the instrument 10', patient name and data transfer date, or by file name. If the "Auto Print" check box is checked, patient reports will be printed upon receipt.

In Phone-In Manager as in Meter Setup Manager, features that are accessed on a routine basis are located in the client area of the window. These features and their data are easily accessible and reviewable. Other features which are used less frequently are located in a standard Microsoft® Windows® menu bar. These include the "File," "View" and "Help" menus. The "File" menu contains commands which operate on patient data. "View Patient Reports" permits the user 24 to view older patient files by selecting the instrument 10' serial number, patient name and date of receipt of data, or the actual file name. "Print Patient Reports" permits the user 24 to print older patient files by selecting the instrument 10' serial number, patient name and date of receipt of data, or the actual file name. "Edit Patient Database" permits the user 24 to add, delete and edit patient name to instrument 10' serial number associations. "Print Setup" is the standard Microsoft® Windows® printer 30 setup routine. "Exit" results in the Phone-In Manager routine being exited.

Figure 54:
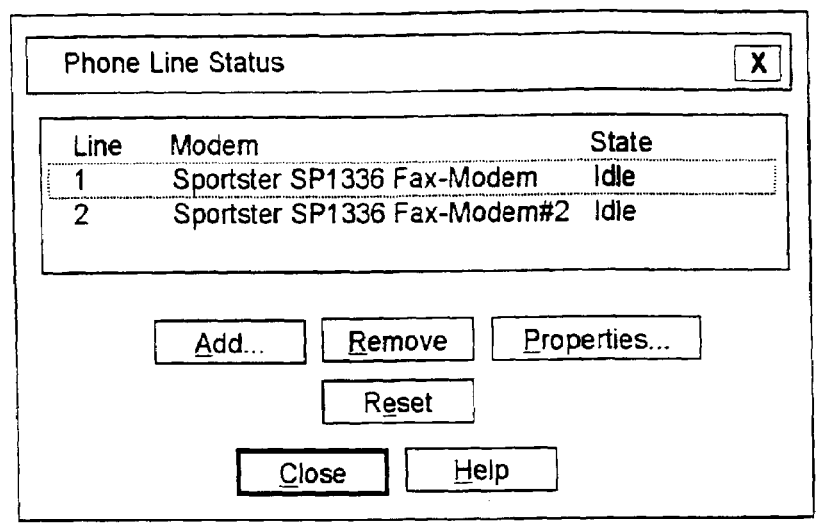
Figure 55:
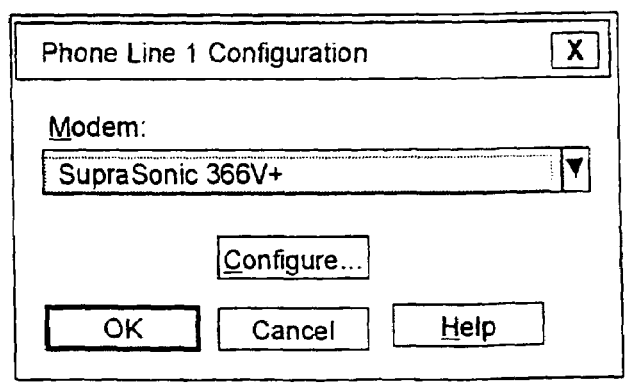

The "View" menu contains menu items that permit the user 24 to view and modify various Phone-In Manager data stores. The "Status Bar" permits the user 24 to turn the status bar at the bottom of the main window on or off. "Phone Line Status" displays a dialog, illustrated in FIG. 54, containing the states of all phone lines. This permits the user 24 to enable or disable one or more of the phone lines 23 connected to the computer 14. When the utility program 12 is running in Windows® 95 and the user 24 clicks on the "Add" button or the "Properties" button on the screen illustrated in FIG. 54, the screen illustrated in FIG. 55 is displayed. This screen permits the user 24 to select from modems 20, 22 configured using the control panel. When the utility program 12 is running in Windows® 3.1 and the user 24 clicks on the "Add" button or the "Properties" button on the screen illustrated in FIG. 54, the screen illustrated in FIG. 56 is displayed. This screen prompts the user 24 to set the serial port and baud rate for the modems 20, 22. When the utility program 12 is running in Windows® 3.1 and the user 24 clicks on the "Advanced Modem Settings" button on the screen illustrated in FIG. 54, the screen illustrated in FIG. 57 is displayed. This screen permits the user 24 to modify modem 20, 22 strings.

Figure 59:
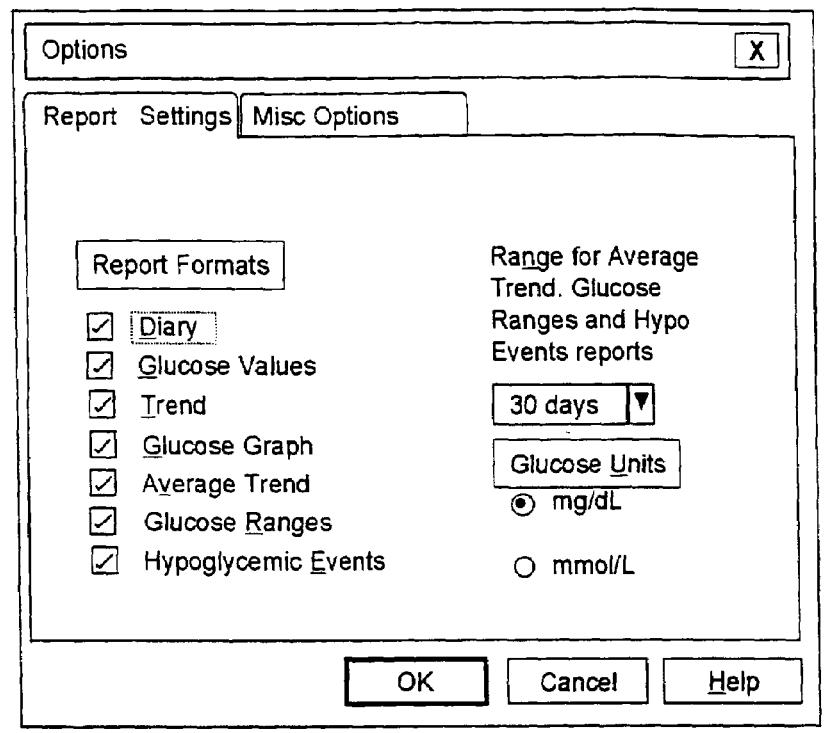
Figure 60:
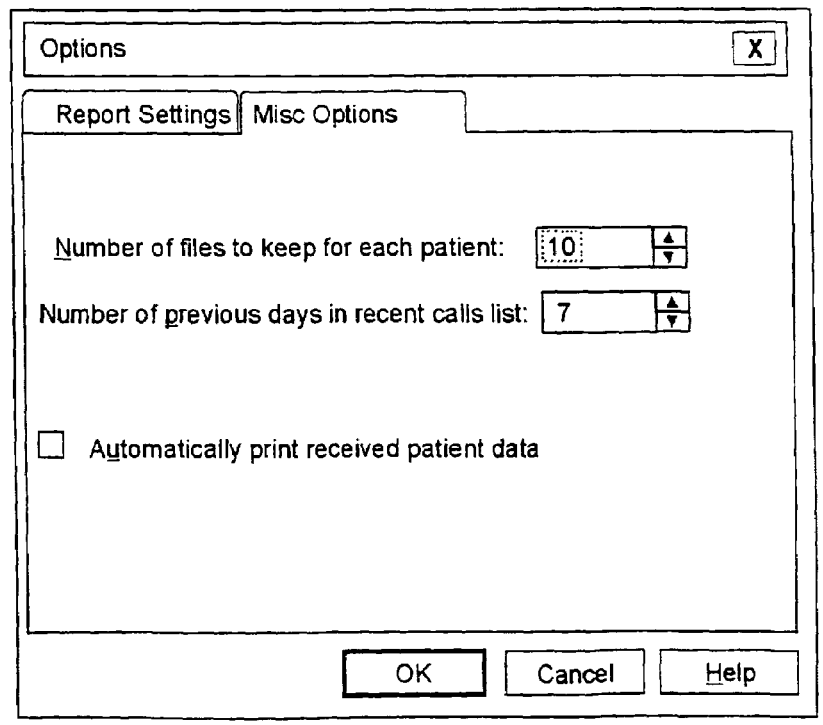

"Call Statistics" causes a screen illustrated in FIG. 58 to be displayed. Statistics for each phone line connected to the computer 14 are displayed. Statistics include the number of calls made to the line, the number of patient data transfers attempted, and the number of patient data transfers which succeeded. This screen also permits the user 24 to reset the statistics. "Options" permits the user 24 to modify the Phone-In Manager options. There are two tabs under "Options." One tab, "Report Settings," is illustrated in FIG. 59. This page permits the user 24 to select the type of Patient Data Report to view. The other tab, "Miscellaneous Options," is illustrated in FIG. 60. This page permits the user 24 to select how many files are kept for each patient, and how many days' calls are kept in the Recent Calls list. It also permits the user 24 to select to have patient reports printed automatically.

The "Help" menu contains items that provide the user 24 with access to information about the Phone-In Manager. "Help Topics" displays the table of contents of a help file. The user 24 may navigate via hyperlinks from the table of contents to the contents of the various help file entries. The "About" entry causes the version of the utility program 12 and copyright notice information to be displayed.

The invention claimed is:

1. A method of configuring a hand-held instrument having on-board circuitry for determining the concentration of a medically significant component of a body fluid or a control and producing an electrical signal representative thereof, the method comprising providing a configuring computer having a first port for transmitting to the hand-held instrument for determining the concentration of the medically significant component of the body fluid or control at least one of instructions for configuring the hand-held instrument for determining the concentration of the medically significant component of the body fluid or control and data for configuring the hand-held instrument for determining the concentration of the medically significant component of the body fluid or control, providing on the instrument a second port for receiving from the configuring computer said at least one of instructions for configuring the hand-held instrument for determining the concentration of the medically significant component of the body fluid or control and data for configuring the hand-held instrument for determining the concentration of the medically significant component of the body fluid or control, connecting said first port directly to said second port, transmitting said one of instructions for configuring the hand-held instrument for determining the concentration of the medically significant component of the body fluid or control and data for configuring said instrument for determining the concentration of the medically significant component of the body fluid or control from said first port directly to said second port, receiving said one of instructions for configuring the hand-held instrument for determining the concentration of the medically significant component of the body fluid or control and data for configuring said instrument for determining the concentration of the medically significant component of the body fluid or control directly from said first port at said second port, and configuring said instrument according to said one of instructions for configuring the hand-held instrument for determining the concentration of the medically significant component of the body fluid or control and data for configuring said instrument for determining the concentration of the medically significant component of the body fluid or control transmitted from said first port and received at said second port.

2. The method of claim 1 wherein providing a configuring computer having a first port for transmitting at least one of instructions for configuring the hand-held instrument for determining the concentration of the medically significant component of the body fluid or control and data for configuring the instrument for determining the concentration of the medically significant component of the body fluid or control comprises providing a configuring computer having a first port for transmitting instructions for configuring the hand-held instrument for determining the concentration of the medically significant component of the body fluid or control, and configuring the instrument in accordance with said instructions.

3. The method of claim 2 wherein providing a configuring computer having a first port for transmitting at least one of instructions for configuring the hand-held instrument for determining the concentration of the medically significant component of the body fluid or control and data for configuring the instrument for determining the concentration of the medically significant component of the body fluid or control comprises providing a configuring computer having a first port for transmitting data for configuring the instrument for determining the concentration of the medically significant component of the body fluid or control, and configuring the instrument in accordance with said data.

4. The method of claim 3 wherein the hand-held instrument further comprises a display for displaying information related to the determined concentration, transmitting said one of instructions for configuring the hand-held instrument for determining the concentration of the medically significant component of the body fluid or control and data for configuring said instrument for determining the concentration of the medically significant component of the body fluid or control from said first port comprising transmitting data for configuring said instrument display.

5. The method of claim 4 further comprising transmitting one of instructions concerning determined concentration of a medically significant component of a body fluid and data concerning determined concentration of a medically significant component of a body fluid from the second port to the first port.

6. The method of claim 5 wherein transmitting one of instructions concerning determined concentration of a medically significant component of a body fluid and data concerning determined concentration of a medically significant component of a body fluid from the second port to the first port comprises transmitting data concerning determined concentration of a medically significant component of a body fluid from the instrument to the computer.

7. The method of claim 6 and further comprising updating a file in the computer with the transmitted data concerning determined concentration of a medically significant component of a body fluid.

8. The method of claim 2 further comprising transmitting one of instructions concerning determined concentration of a medically significant component of a body fluid and data concerning determined concentration of a medically significant component of a body fluid from the second port to the first port.

9. The method of claim 8 wherein transmitting one of instructions concerning determined concentration of a medically significant component of a body fluid and data concerning determined concentration of a medically significant component of a body fluid from the second port to the first port comprises transmitting data concerning determined concentration of a medically significant component of a body fluid from the instrument to the computer.

10. The method of claim 9 and further comprising updating a file in the computer with the transmitted data concerning determined concentration of a medically significant component of a body fluid.

11. The method of claim 3 further comprising transmitting one of instructions concerning determined concentration of a medically significant component of a body fluid and data concerning determined concentration of a medically significant component of a body fluid from the second port to the first port.

12. The method of claim 11 wherein transmitting one of instructions concerning determined concentration of a medically significant component of a body fluid and data concerning determined concentration of a medically significant component of a body fluid from the second port to the first port comprises transmitting data concerning determined concentration of a medically significant component of a body fluid from the instrument to the computer.

13. The method of claim 12 and further comprising updating a file in the computer with the transmitted data concerning determined concentration of a medically significant component of a body fluid.

14. The method of claim 2 wherein the hand-held instrument further comprises a display for displaying information related to the determined concentration, transmitting instructions for configuring the hand-held instrument for determining the concentration of the medically significant component of the body fluid or control from said first port to configure said instrument comprising transmitting instructions for configuring the hand-held instrument for determining the concentration of the medically significant component of the body fluid or control for configuring said display.

15. The method of claim 14 further comprising transmitting one of instructions concerning determined concentration of a medically significant component of a body fluid and data concerning determined concentration of a medically significant component of a body fluid from the second port to the first port.

16. The method of claim 15 wherein transmitting one of instructions concerning determined concentration of a medically significant component of a body fluid and data concerning determined concentration of a medically significant component of a body fluid from the second port to the first port comprises transmitting data concerning determined concentration of a medically significant component of a body fluid from the instrument to the computer.

17. The method of claim 16 and further comprising updating a file in the computer with the transmitted data concerning determined concentration of a medically significant component of a body fluid.

18. The method of claim 1 wherein providing a configuring computer having a first port for transmitting at least one of instructions for configuring the hand-held instrument for determining the concentration of the medically significant component of the body fluid or control and data for configuring the instrument for determining the concentration of the medically significant component of the body fluid or control comprises providing a configuring computer having a first port for transmitting data for configuring the instrument for determining the concentration of the medically significant component of the body fluid or control, and configuring the instrument in accordance with said data.

19. The method of claim 18 further comprising transmitting one of instructions concerning determined concentration of a medically significant component of a body fluid and data concerning determined concentration of a medically significant component of a body fluid from the second port to the first port.

20. The method of claim 19 wherein transmitting one of instructions concerning determined concentration of a medically significant component of a body fluid and data concerning determined concentration of a medically significant component of a body fluid from the second port to the first port comprises transmitting data concerning determined concentration of a medically significant component of a body fluid from the instrument to the computer.

21. The method of claim 20 and further comprising updating a file in the computer with the transmitted data concerning determined concentration of a medically significant component of a body fluid.

22. The method of claim 1 wherein the hand-held instrument farther comprises a display for displaying information related to the determined concentration, transmitting said one of instructions for configuring the hand-held instrument for determining the concentration of the medically significant component of the body fluid or control and data for configuring said instrument for configuring the hand-held instrument for determining the concentration of the medically significant component of the body fluid or control from said first port comprising transmitting said one of instructions for configuring the hand-held instrument for determining the concentration of the medically significant component of the body fluid or control and data for configuring the hand-held instrument for determining the concentration of the medically significant component of the body fluid or control from said first port to configure said display.

23. The method of claim 22 further comprising transmitting one of instructions concerning determined concentration of a medically significant component of a body fluid and data concerning determined concentration of a medically significant component of a body fluid from the second port to the first port.

24. The method of claim 23 wherein transmitting one of instructions concerning determined concentration of a medically significant component of a body fluid and data concerning determined concentration of a medically significant component of a body fluid from the second port to the first port comprises transmitting data concerning determined concentration of a medically significant component of a body fluid from the instrument to the computer.

25. The method of claim 24 and further comprising updating a file in the computer with the transmitted data concerning determined concentration of a medically significant component of a body fluid.

26. The method of claim 1 further comprising transmitting one of instructions concerning determined concentration of a medically significant component of a body fluid and data concerning determined concentration of a medically significant component of a body fluid from the second port to the first port.

27. The method of claim 26 wherein transmitting one of instructions concerning determined concentration of a medically significant component of a body fluid and data concerning determined concentration of a medically significant component of a body fluid from the second port to the first port comprises transmitting data concerning determined concentration of a medically significant component of a body fluid from the instrument to the computer.

28. The method of claim 27 and further comprising updating a file in the computer with the transmitted data concerning determined concentration of a medically significant component of a body fluid.

29. The method of claims 1, 2, 3, 18, 22, 14 or 4 wherein transmitting said one of instructions for configuring the hand-held instrument for determining the concentration of the medically significant component of the body fluid or control and data for configuring said instrument for determining the concentration of the medically significant component of the body fluid or control from said first port and receiving said one of instructions for configuring the hand-held instrument for determining the concentration of the medically significant component of the body fluid or control and data for configuring said instrument for determining the concentration of the medically significant component of the body fluid or control at said second port comprise transmitting said one of instructions for configuring the hand-held instrument for determining the concentration of the medically significant component of the body fluid or control and data for configuring said instrument for determining the concentration of the medically significant component of the body fluid or control through a fiber optic coupler from said first port to said second port.

30. The method of claim 29 wherein the instrument for determining the concentration of the medically significant component of the body fluid or control comprises an instrument for determining the glucose concentration of blood, a blood fraction or a control.

31. The method of claims 26, 27, 28, 8, 9, 10, 11, 12, 13, 19, 20, 21, 23, 24, 25, 15, 16, 17, 5, 6 or 7 wherein transmitting said one of instructions concerning determined concentration of a medically significant component of a body fluid and data concerning determined concentration of a medically significant component of a body fluid from the second port to the first port comprises transmitting said one of instructions concerning determined concentration of a medically significant component of a body fluid and data concerning determined concentration of a medically significant component of a body fluid via a modem from the second port to the first port.

32. The method of claim 31 wherein the instrument for determining the concentration of the medically significant component of the body fluid or control comprises an instrument for determining the glucose concentration of blood, a blood fraction or a control.

* * * * *